United States Patent [19]

Mujumdar et al.

[11] Patent Number: 5,981,747

[45] Date of Patent: Nov. 9, 1999

[54] MONOMETHINE CYANINES RIGIDIZED BY A TWO-CARBON CHAIN

[75] Inventors: Ratnakar B. Mujumdar, Glenshaw; Alan S. Waggoner, Pittsburgh, both of Pa.; Bhalchandra M. Karandikar, Tigard, Oreg.

[73] Assignee: Carnegie Mellon University, Pittsburgh, Pa.

[21] Appl. No.: 08/997,275

[22] Filed: Dec. 23, 1997

Related U.S. Application Data

[63] Continuation of application No. 08/474,057, Jun. 7, 1995.
[51] Int. Cl.$^6$ .................................................. C07D 495/22
[52] U.S. Cl. ............................................................ 540/555
[58] Field of Search ............................................. 540/555

[56] References Cited

U.S. PATENT DOCUMENTS

| | | | |
|---|---|---|---|
| 2,432,080 | 12/1947 | Anish | 268/540 |
| 2,541,400 | 2/1951 | Brooker et al. | 266/240.7 |
| 3,148,187 | 9/1964 | Heseltine | 260/240.4 |
| 3,250,780 | 5/1966 | Rai et al. | 260/307 |
| 3,729,467 | 4/1973 | Zweldler et al. | 260/240.7 |
| 4,064,136 | 12/1977 | Lowe et al. | 260/304 |
| 4,337,063 | 6/1982 | Mihara et al. | 23/230 B |
| 4,404,289 | 9/1983 | Masuda et al. | 436/538 |
| 4,405,711 | 9/1983 | Masuda et al. | 435/4 |
| 4,774,339 | 9/1988 | Haugland et al. | 548/405 |
| 4,916,711 | 4/1990 | Bayer et al. | 372/53 |
| 5,187,288 | 2/1993 | Haugland et al. | 548/427 |
| 5,248,782 | 9/1993 | Hauland et al. | 548/427 |
| 5,268,486 | 12/1993 | Waggoner et al. | 548/427 |
| 5,274,113 | 12/1993 | Kang et al. | 548/110 |

FOREIGN PATENT DOCUMENTS

| | | |
|---|---|---|
| 1573139 | 7/1969 | France . |
| 610064 | 10/1948 | United Kingdom . |
| 618889 | 3/1949 | United Kingdom . |
| 1529202 | 10/1978 | United Kingdom . |
| PCT/US92/ 08350 | 5/1993 | WIPO . |

OTHER PUBLICATIONS

Shah et al. Pyrromethene–BF$_2$ Complexes as Laser Dyes: 1., *Heteroatom Chemistry* (vol. 1, No. 5, 1990).
Kaplan et al., "Synthesis and Luminescense—Spectral Characteristics of the Chelates of Boron with Diheterylamines" (1991) translated from *Zhurnal Organicheskai Khimii*, vol. 27, No. 4, pp. 872–877, Apr. 1991.
Kang and Haugland, "Spectral Properties of 4–Sulfonato–3, 3',5'5'—Tetramethyl–22'—Pyrromethen–1,1'—Barandifluoride Complex (Bodipy), Its Sodium Salt, and Protein Derivatives," SPIE, vol. 1063 *New Technologies in Cytometry* (1989), pp. 68–73.
Douglass et al., "Diazobarayclic Cations. III. A Homomorph of 9, 10–Dihydroanthracene (1)," *Journal of Heterocyclic Chemistry* (vol. 10, 1973), pp. 255–257.
Scheibe and Daltrozzo, *Advances in Heterocyclic Chemistry*, vol. 6, pp. 153–181 (Academic Press 1965).
Ramos et al., "Crystal and Molecular Structure of 6–Phenyl–13H–Pyrimido [4,3–B:6,1–b] bis–benzothiazoluim–12 triiodide," *J. of Crystallographic and Spectroscopic Research*, vol. 21, No. 2, 1991, pp. 179–182.
Abbotto, "Novel Heteroaromatic and Heteroalicyclic Metal Methanates, [ML$_2$ {L=Bis(2–Benzothiazolyl) and Bis [2–($\Delta^2$–Tiazolinyl)]}", Gazzettia Chimica Italiana, 121, 1991, pp. 303–305.
Hugel, A Facile Synthesis of (+)2–(4–Chlorophenyl)–a–Methyl–5–Benzoxazoleacetic Acid (Benoxaprofen) Comm. 15, pp. 1075–1080 (1985).
Muller et al., 21.C$_2$–Symmetric 4,4',5,5'-Tetrahydrobi (oxazoles) and 4,4',5,5'—Tetrahydro–2,2–'methylenebis [oxazoles] as Chiral Ligands for Enantioselective Catalysis, Hel, Chim. Acta, 74, 232–240 (1991).
Hamer, *The Cyanine Dyes and Related Compounds* (John Wiley & Sons, New York 1964), pp. 32–85.
Ramos et al., "Reactivity of Aryl–and Heteroarylmalonates against ortho–Dunicleophiles. Triaryl (heteroaryl) methane Synthesis", *J. Hetero. Chem. 24*, 247 (1987).
van Koeveringe et al., Novel pyrromethenes 1–Oxygen and 1–sulfer analogues; evidence for photochemical Z–E isomerization, Recl. Trav. Chim. Pas–Bas, vol. 96, p. 55.
Lapworth et al., Oxidation Products of Oleic Acid. Part I. Conversion of Oleic Acid into Dihydroxystearic Acid and the Determination of the Higher Saturated Acids in Mixed Acids from Natural Sources, J. Chem. Soc., 1628 (1925).
Saito, et al., Combination of Borane–Dimethyl Sulfide Complex With Catalytic Sodium Tetrahydroborate as a Selective Reducing Agent For a–Hydroxy Esters, Versatile Chiral Building Block from (s)–(–) Malic Acid, Chem. Letters, 1389–1392 (1984).
Newkone, et al., Nitrile–Stabilized Carbanions. Nucleophilic Substitution Reactions on Bromopyridines, J. Org. Chem., 1988, 53, 786–780.
Saiot, et al., Synthetic Studies Using a B–Unsaturated Mitriles: A Convenient Preparation of 1,3–Bezothiazole Derivatives, Synthesis, (3), pp. 210–211 (1983).

(List continued on next page.)

*Primary Examiner*—Richard L. Raymond
*Assistant Examiner*—Pavanaram K Sripada
*Attorney, Agent, or Firm*—Kirkpatrick & Lockhart LLP

[57] ABSTRACT

Fluorescent monomethine cyanine complexes rigidized by a two-carbon alkyl group between the nitrogen's of the cyanine's heterocycles are provided and have the structure

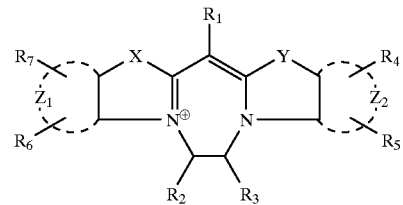

wherein $R_1$ through $R_7$ represent various selected groups or ring structures that may be chosen to provide desired solubility, reactive, or spectral properties.

4 Claims, 3 Drawing Sheets

OTHER PUBLICATIONS

McElvain, et al., Orthoesters and Related Compounds from Malono–and Succinonitriles, JACS, vol. 71, pp. 40–46 (1949).

Ramos, et al., Tautomerism of Bis (2–Benzothiazolyl)Arylmethanes, Heterocycles, vol. 29, No. 1, pp. 165–180 (1989).

Avendano et al., Tautomerism of bis (2–Benzothiazolyl) methanes, Can. J. Chem., vol. 67, pp. 1467–1473 (1988).

Vos de Wael, et al., Pyrromethene–BF$_2$complexes (4,4'–difluoro–4–bora–3a, 4a–diaza–s–indacenes). Synthesis and luminescence properties, Recl. Trav. Chim. Pay–Bas, vol. 96, p. 306 (1977).

Wories, et al., A novel water–soluble fluorescent probe: Synthesis, luminescence and biological properties of the sodium salt of the 4–sulfonato–3,3',5,5'–tetramethyl–2, 2'–pyrromethen–1,1'BF$_2$complex, Recl. Trav. Chim. Pays–Bas 104, 288–291 (1985).

Treibs, et al., Difluorboryl–Komplexe von Di–und Tripyrrylmethen, Liebigs Ann. Chem., vol. 718, pp. 208–223 (1968).

*Bodipy: The New Fluorescein Substitute,* Bioprobes, No. 10, (Molecular Probes, Inc., Eugene, Or.) (Dec. 1989).

*Reactive Bodipy Dyes,* (Molecular Probes, Inc., Eugene, OR 1992), pp. 1–3.

D.M.Sturmer and W.S. Gaugh, "Spectral Sensitization by Sterically Hindered Chromophores", Photographic Science and Engineering, vol. 19, No. 5 (Sep.–Oct. 1975), pp. 275–278.

T. Ramos et al., "Crystal and molecular structure of 6—phenyl–13H–pyrimido [4,3–6: 6, 1—b] bis–benzothiazolium—12 trliodide, " J. Crystallographic and Spectroscopic Research, vol. 21, No. 2 (Apr. 1991), pp. 179–182.

C. Scheibe et al., "Das Franck–condon–Prinzip und die Lichtabsorpotion von Merocyaninen", Z. physik, Chem. Neue Folge, Bd. 64, S. 97–114 (1969).

C. N. McEwen et al., "Field Desorption and Election Impact Mass Spectra of Ionic Dyes", *Analytical Chemistry,* vol. 49, No. 7, Jun. 1977.

MONOMETHINE CYANINES RIGIDIZED BY A TWO-CARBON CHAIN

This a continuation of copending U.S. patent application Ser. No. 08/474,057, filed on Jun. 7, 1995.

This invention was made with government support under Contract NSF-DIR-8920118 awarded by the Public Health Service of the United States Department of Health and Human Services.

BACKGROUND OF THE INVENTION

1. Field of the Invention

The present invention relates to chemical dyes which can be used as fluorescent markers. The present invention particularly relates to fluorescent monomethine cyanine-based compounds which have been sterically rigidized by the inclusion of a bridging two-carbon alkyl group between the compound's heterocyclic groups and which may be chemically modified to include chemical moieties to allow the compounds to covalently or noncovalently associate with a material to thereby impart fluorescent properties to the material.

2. Description of the Invention Background

Fluorescent dyes are generally known for imparting fluorescence to biological and nonbiological materials and have been used to detect various biological or other materials by procedures such as fluorescence microscopy, fluorescence immunoassay techniques, and flow cytometry. The primary advantages of fluorescent dyes compared with dyes detectable only through light absorption include (i) the emission of light by fluorescent dyes at a wavelength different from their excitation wavelength; (ii) the greatly enhanced detectability of fluorescence emission compared to light absorption; and (iii) the generally minimal level of background fluorescence in most biological materials.

A common method for labeling biological and nonbiological materials with fluorescent dyes is to create a fluorescent complex through covalent bonding between groups on the dye molecules and compatible groups on the material. In this way, materials such as, for example, cells, tissues, amino acids, proteins, antibodies, enzymes, drugs, hormones, nucleotides, nucleic acids, polysaccharide, and lipids may be chemically labeled and quantified or may be used as fluorescent probes that bind specifically to target materials (genetic sequences, haptens, antibodies, analytes, etc.) that are to be detected by fluorescence methods. Polymer particles, cells, and other materials labeled with fluorescent dyes can also be used as fluorescent standards in flow cytometers, imaging microscopes, and other fluorescence-based detection equipment. Minute fluorescent polymer particles can also be used as labels in immunofluorescence tests, toxicology testing, and analysis of genetic sequences. Because of their utility in research and medicine, a large market has developed for fluorescent reagents including prepared protein, antibody, and nucleic acid, and other probes pre-labeled with detectable fluorescent or fluorescent dye compounds.

Because most dye molecules are either nonfluorescent or only weakly fluorescent, available fluorescent dye markers have been derived from a relatively limited number of fluorescent aromatic structures. New fluorophores with optimal properties are rarely developed. Two common classes of fluorescent dyes are those derived from the fluorescein and rhodamine chromophores. Fluoresceins fluoresce green light whereas rhodamines fluoresce in the green-orange and red regions of the spectrum. The rhodamines are difficult labeling reagents to use, are not particularly fluorescent when bound to proteins, and often cause the precipitation of the labeled protein when the dye-to-protein ratio is greater than 2:1. One particular fluorescein dye, fluorescein isothiocyanate ("FITC"), and its conjugates, enjoy wide acceptance primarily because they have a relatively high extinction coefficient and have a high quantum yield. (Quantum yield is generally related to a molecule's rigidity or planarity and indicates the molecule's propensity to fluoresce, i.e., give off energy as light, rather than give off heat when energy is provided to the molecule.) However, fluorescein dyes have a number of disadvantages, including their strong tendency to photobleach when illuminated by a strong excitation source such as the lamps used in fluorescence microscopes. When a fluorescent compound photobleaches, a large percentage of the compound's fluorescence may be lost within seconds of illumination, resulting in a rapidly diminishing image. Also, when performing fluorescence assays, the loss of image through time by photobleaching makes quantifying results much more difficult and will ultimately result in a decreased ability to detect the analyte. Reagents, such as propyl gallate and p-phenylene-diamine, may retard but do not entirely eliminate photobleaching. The fluoresceins also have a pH-sensitive absorption spectrum and fluorescence yield decreases below pH 8 and the fluoresceins do not fluoresce at low pH.

Multiple fluorophores of different colors are used simultaneously in multi-parameter analyses for detecting and correlating different fluorescently-labeled materials in such procedures as flow cytometry, microscopy, chromatography and various other detection systems. In multi-parameter analyses, a number of fluorescent compounds having a binding affinity for different targets and having different maximum emission wavelengths are used to detect and quantify the sample's various targets. To reduce the overlap of fluorescence signals in multi-parameter analyses that are emitted from the target materials labeled with different fluorescent compounds, it is desirable to use fluorescent compounds with narrow absorption and emission bands.

One class of blue-fluorescing dyes, the coumarins, suffer from a number of disadvantages. For example, the coumarin-based fluorophore 7-amino-4-methylcoumarin acetate has broad absorption and emission peaks, Also, this compound has a relatively low extinction coefficient of approximately 17,000 l/mol-cm (Handbook of Fluorescent Probes and Research Chemicals, Molecular Probes Inc., Eugene, Ore.), thereby providing a fluorescence capacity (equal to the mathematical product of the extinction coefficient and the quantum yield) of approximately one-quarter that of the present inventions' compounds. Similarly, a fluorescent labeling dye available from Molecular Probes, Inc., under the trade name Cascade Blue (having the structure shown below where R is a reactive group) has an extinction coefficient of only 29,000 l/mol-cm.

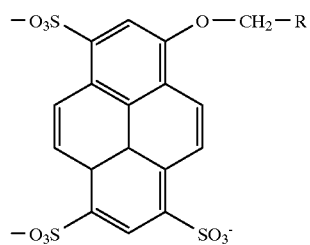

The cyanine compounds are now recognized as fluorescent labeling dyes. Cyanines generally include two heterocyclic groups connected by a chain of conjugated double bonds with an odd number of carbon atoms and have been used as spectral sensitizers for photographic film. Cyanine compounds are utilized as spectral sensitizers in, for example, U.S. Pat. Nos. 4,337,063 (Miraha et al.) and 4,404,289 (Masuda et al.), 4,405,711 (Masuda et al.), and British Patent No. 1,529,202 (Exekial et al.). Fluorescence is not necessary for the photographic applications in those patents and fluorescent properties are not mentioned in those patents. The utility of cyanine compounds as fluorescent dyes was discovered only recently.

Cyanine compounds known to be useful fluorescent dyes include the unrigidized, arylsulfonated cyanine compounds of U.S. Pat. No. 5,268,486 to Waggoner et al, having the following general structure:

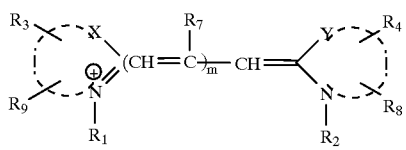

wherein, the dotted lines represent one to three rings having five to six atoms in each ring. $R_3$, $R_4$, $R_8$ and $R_9$ groups are attached to the rings. At least one of the $R_8$ and $R_9$ groups is a sulfonic acid or sulfonate group and at least one of the $R_1$, $R_2$, $R_3$, $R_4$ and $R_7$ groups is a moiety that will react with amino, hydroxy, phosphoryl, or sulfhydryl groups. The Waggoner et al. patent relates to trimethine, pentamethine, etc., cyanines (i.e., cyanines with more than a single double bond in the conjugated chain) and which fluoresce in the green, orange, red and near-infrared regions of the spectrum. Cyanines of this type have not been considered useful covalent labels.

One class of the cyanines includes a single atom bridging the heterocycles. These compounds are referred to herein as "rigidized" cyanines because the bridging atom restricts movement of the heterocycles about the conjugated carbon atom chain. Certain rigidized cyanines have been developed for photographic sensitization. See U.S. Pat. Nos. 2,541,400 to Brooker et al. and 3,148,187 to Heseltine. These cyanines cannot be used as fluorescent labeling dyes.

A class of monomethine cyanine-type compounds having a single atom of boron bridging the cyanine's heterocyclic groups is disclosed as useful fluorescent marker compounds in pending U.S. patent application Ser. No. 08/474,056 entitled "Rigidized Monomethine Cyanines" filed on Jun. 7, 1995, the entire disclosure of which is hereby incorporated herein by reference.

Considering the above, but for the compounds disclosed in the above pending application, the existing compounds recognized as fluorescent markers suffer from several disadvantages. Also, although certain rigidized cyanine complexes are known, the majority have not been evaluated for their suitability as fluorescent dye markers.

Accordingly, it is an object of the present invention to provide bright, highly fluorescent, strongly light absorbing dyes that can be used to covalently or noncovalently associate with a material to impart fluorescent properties to the material.

It is also an object of the invention to provide fluorescent markers having high quantum yields and extinction coefficients, and therefore high fluorescence, compared with available fluorescent marker compounds, and that are relativity insensitive to pH.

It is a further object of the present invention to provide fluorescent markers that are relatively photostable, have sharp and distinct absorption and emission maxima, and have relatively small stokes shifts.

It is also an object of the present invention to provide fluorescent compounds having a short resonance distance relative to the existing fluorescent cyanine compounds so that the compounds of the present invention may have maximum absorptive and/or emissive wavelengths in the blue spectral region below 500 nm.

An additional object of the present invention is to provide a fluorescent compound having a general chemical structure that is easily modified by the addition or substitution of chemical moieties to, for example, modify the compound's emissive and absorptive maxima and solubility in polar and nonpolar media, change the reactivity of the compound, and covalently or noncovalently associate the compound with a material.

SUMMARY OF THE INVENTION

To satisfy the above objectives, the present invention relates to monomethine cyanine complexes that have been rigidized by the inclusion of a bridging two-carbon alkyl group between the nitrogens of the cyanine's heterocycles, that can be prepared by the processes generally described below, and that have the following structure:

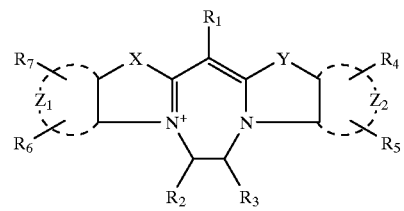

wherein groups $R_1$ through $R_7$ are chosen to provide desired solubility, reactivity, and spectral properties to the fluorescent compound. Such groups $R_1$ through $R_7$ include —P and —W—P wherein P may, for example, be selected from:

neutral groups that reduce water solubility selected from, for example, hydrogen and the halogen atoms;

polar groups that increase water solubility selected from, for example, amide, sulfonate, sulfate, phosphate, quaternary ammonium, hydroxyl and phosphonate;

functional groups that can be used in labeling reactions selected from, for example, amino, hydroxyl, sulfhydryl, carboxyl and carbonyl groups;

reactive groups selected from, for example, succinimidyl ester, isothiocyanate, isocyanate, iodoacetamide, maleimide, sulfonyl halide, phosphoramadite, alkylimidate, arylimidate groups, acid halide, substituted hydrazines, substituted hydroxylamines, carbodiimides; and electron donating and withdrawing groups that shift the absorption and emission wavelengths of the fluorescent molecule.

Electron withdrawing groups include groups such as, fore example, cyano, nitro, fluoromethyl, amide, nitrophenyl, sulfonamide, alkenyl, and alkynyl groups.

W is a linker chain of atoms and may be, for example, a straight or branched alkyl chain of 1–27 carbon atoms, monoethers containing 2–20 carbon atoms, and polyethers containing 2–20 carbon atoms. Dotted lines $Z_1$ and $Z_2$ represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur and $R_4$, $R_5$, $R_6$ and $R_7$ are optionally attached to the atoms of the $Z_1$ and $Z_2$ ring structures.

More particularly, and with reference to the above figure, the rigidized monomethine cyanine complexes of the present invention are those wherein:

X and Y are selected from —$C(CH_3)_2$, oxygen, sulfur, selenium, CH=CH, and N—W wherein N is nitrogen and W is selected from hydrogen, alkyl groups of twenty-six carbons or less, —$(CH_2)_nP$ where 1<n<26 and P is selected from amino, aldehyde, acetal, ketal, halogen, cyano, aryl, heteroaryl, hydroxyl, sulfonate, sulfate, carboxylate, substituted amino, quaternary amino, nitro, substituted aryl, substituted heteroaryl, primary amide, substituted amide, and groups reactive with amino, hydroxyl, aldehyde, phosphoryl, or sulfhydryl groups;

dotted lines $Z_1$ and $Z_2$ optionally represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur;

$R_4$ through $R_7$ are attached to the five-membered heteroatom rings containing X and Y or, optionally, are attached to atoms of the $Z_1$ and $Z_2$ ring structures and each $R_4$ through $R_7$ is selected from hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, —E—F where F is hydroxy, sulfonate, sulfate, carboxylate, substituted amino or quaternary amino, and where E is a spacer group selected from —$(CH_2)_n$— where n is 0, 1, 2, 3, 4, or 5, and groups reactive with amino, hydroxyl, aldehyde, phosphoryl or sulfhydryl groups;

$R_2$ and $R_3$ are selected from the same groups possible for $R_4$ through $R_7$; and $R_1$ is selected from hydrogen, aryl, substituted aryl, heteroaryl, substituted heteroaryl, cyano, nitro, aldehyde, halogen, hydroxy, alkyl groups of twenty-six carbons or less, amino, quaternary amino, acetal, ketal, phosphoryl, sulfhydryl, water-solubilizing groups, and —$(CH_2)_nQ$ where 1<n<26 and Q is selected from amino, substituted amino, quaternary amino, aldehyde, acetal, ketal, halogen, cyano, aryl, substituted aryl, heteroaryl, substituted heteroaryl, hydroxyl, sulfonate, sulfate, carboxylate, amide, nitro, and groups reactive with amino, hydroxyl, aldehyde, phosphoryl, or sulfhydryl groups.

For particular applications such as laser dye applications, it may be desirable that the structure does not include chemical groups attached thereto and that each of $R_1$, $R_2$, $R_3$, $R_4$, $R_5$, $R_6$ and $R_7$ are hydrogen atoms. Therefore, unsubstituted compounds of the present invention useful for laser dye applications include the following:

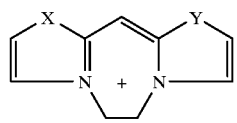
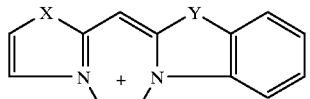
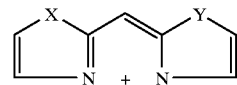
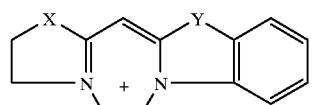
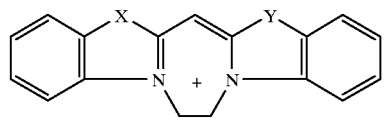
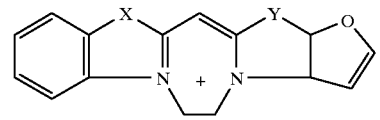
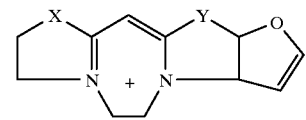

The structural differences between the compounds of the present invention and the nonrigidized cyanines are apparent. It has been found that unrigidized monomethine cyanines tend to be nonfluorescent unless excited in an environment which maintains the molecule in a rigid posture. It is believed that thermal flexation of a monomethine cyanine's heterocyclic groups about the monomethine bridge may deactivate the molecule's excited state before fluorescence can occur. It has been found that rigidization of the cyanine structure results in greatly enhanced fluorescence without stearic hindrance of the numerous molecular positions available for the attachment of solubilizing, nucleophilic, reactive, or other groups. It is believed that rigidization between the heterocycles of the cyanine molecule inhibits the movement of the heterocycles about the bridging conjugated carbon atom when the molecule absorbs energy and a greater part of the energy absorbed by a rigidized molecule is re-emitted as light energy rather than heat relative to an unrigidized molecule.

The increase in fluorescence derived from rigidization is demonstrated by FIG. 1 showing the relative fluorescence spectra of a rigidized monomethine cyanine (curve a), an unrigidized N,N'-dimethyl-di-2-benzothiazolyl methane in glycerol (curve b), and the same unrigidized molecule in water (curve c). All samples were excited at 364 nm. The 640,000 cps relative intensity of the rigidized molecule at the maximum emission wavelength (400 nm) is several times greater than the unrigidized molecule in bath glycerol (200,000 cps) and water (10,000 cps). Also, it is believed that the un-rigidized species has much greater intensity in glycerol than water because the glycerol sterically rigidizes the molecule to a much greater extent than water. The present inventors have determined that the rigidization of the basic monomethine cyanine structure increases the quantum efficiency of the dye molecules as much as 5–20 times. Thus, the carbon-rigidized dyes of the present invention are unusually fluorescent compared with the non-rigidized cyanine dye molecules.

Compared with, for example, the fluoresceins, the carbon-rigidized monomethine cyanines of the present invention are particularly photostable and are insensitive to pH changes between pH 2 and pH 10. Certain of the compounds of the present invention maximally absorb and emit light at wavelengths between 400 and 500 nm and less, and are therefore alternatives to conventional fluoresceins and rhodamines. Also, the present invention's approximate 400–500 nm emission maxima corresponds to the "blue" region of the visible spectrum and is therefore generally lower than the known BODIPY compounds, quinoline-based monomethine cyanine complexes, and pyridine-based monomethine cyanine complexes, which have absorption and emission maxima of 500 nm or greater and fluoresce in the "green" region.

The present inventors have concluded that it is the number of conjugated double bonds and the corresponding resonance distance which is the major influence on the maximum absorption and emission wavelengths of the fluorescent compound. It is believed that the low maximum absoprtion and emission wavelengths of the present compounds relative to those that fluoresce in the "green" region of the spectrum results from the short conjugated double bond resonance path of the present invention's compounds. The present inventors have also found that the maximum emissive wavelength of fluorescent cyanine compounds can be increased by attaching additional fused ring structures or heteroatoms to the cyanine's heterocycles. By slightly modifying the general chemical structure of the present invention, a number of fluorescent compounds may be provided having different maximum emission wavelengths. The various different markers can be used in, for example, multi-parameter fluorescence studies to detect the presence of numerous target molecules in a mixture. Each different marker will react with a different target and disclose the target's presence by fluorescing at a characteristic wavelength.

The carbon-rigidized monomethine cyanine complexes of the present invention are also highly fluorescent, having quantum yields greater than 0.5 and extinction coefficients approximating 90,000 liters/mole-centimeter. The carbon-rigidized monomethine cyanine complexes of the present invention also have sharp and distinct absorption and emission maxima, a small Stokes shift, and are relatively photostable such that their emissive signals do not fade when they are illuminated in a detection system. For purposes of the present specification, the Stokes shift of a fluorescent compound is the absolute difference in nm between the compounds maximum absorptive and emissive wavelengths. Importantly, the compounds of the present invention may be easily synthesized by the methods disclosed herein. Derivatives of the compounds having a particular utility are easily prepared by modifying the basic compound by a number of methods to include functional groups at a variety of positions. As examples, the complexes of the present invention may be modified to include certain reactive groups for preparing a fluorescent labeling reagent, or charged or polar groups may be added to enhance the water solubility of the fluorophore.

The compounds of the present invention may be used in numerous biological and nonbiological applications. With respect to nonbiological applications, compounds of the present invention having one or more uncharged groups at the $R_1$ through $R_7$ positions, for example, alkyl and aryl moieties of twenty-six carbon atoms or less, may be dissolved in nonpolar materials to provide fluorescent properties to those materials. Such nonpolar materials include, for example, paints, polymers, waxes, oils, inks and hydrocarbon solvents. Another nonbiological application of the present invention is to dissolve compounds of the present invention having one or more charged and/or polar groups at the $R_1$ through $R_7$ positions in polar solvents or other materials such as, for example, water, methyl alcohol, or a mixture of water and methyl alcohol. Such charged R-groups include, for example,

$—SO_3^-$, $—PO_3^-$ and $—COO^-$, while such polar R-groups include, for example, hydroxyl groups.

With respect to biological applications, biological molecules may be noncovalently labeled using the present invention's compounds. For example, compounds of the present invention wherein at least one of $R_1$ through $R_7$ are charged groups such as, for example, amino and quaternary amino, may be used to noncovalently bind to charged biological molecules such as, for example, DNA and RNA. In addition, compounds of the present invention wherein at least one of $R_1$ through $R_7$ is an uncharged group such as, for example, a long chain alkyl, may be used to covalently bind to uncharged biological molecules such as, for example, biological lipids.

An additional application of the compounds of the present invention is the covalent labeling of a target material to impart fluorescent properties to the target material. Covalent labeling using the present invention's compounds may be either a biological or a nonbiological application depending on the particular application. Examples of target materials that may be covalently labeled in nonbiological applications include, for example, cellulose-based materials (including, for example, papers), textiles, petroleum-based products, photographic films, glasses, polymers and gel filtration and chromatography media.

Covalent labeling by the present invention's compounds may be accomplished in two ways. In a first procedure, a target material having at least one functional group selected from amino, hydroxyl, carbonyl, phosphoryl and sulfhydryl groups may be incubated with an amount of a compound of the present invention having at least one of $R_1$ through $R_7$ that is a reactive group that can covalently bind with the target material's functional group. The target material and the compound of the present invention are incubated under conditions and for a period of time sufficient to permit the reactive group of the fluorescent compound to covalently bond to the functional group of the target material. In an alternate procedure for imparting fluorescent properties to a target, an amount of a fluorescent compound of the present invention wherein at least one of $R_1$ through $R_7$ is a functional group selected from amino, hydroxyl, phosphoryl, carbonyl, and sulfhydryl groups is incubated with a target material having at least one reactive group that can covalently bind with the functional group of the fluorescent compound. The target material and the compound of the present invention are incubated under conditions and for a period of time sufficient to permit the reactive group of the target material to covalently bond to the functional group of the present invention's compound.

The rigidized monomethine cyanine complexes of the present invention also have sharp and distinct absorption and emission maxima, a small Stokes shift, and are relatively photostable such that their emissive signals do not fade when they are illuminated in a detection system. For purposes of the present specification, the Stokes shift of a fluorescent compound is the absolute difference in nanometers between the compound's maximum absorptive and emissive wavelengths. Importantly, the rigidized complexes of the present invention may be synthesized by the methods disclosed herein. Derivatives of the compounds having a particular utility are prepared either by selecting appropriate precursors or by modifying the resultant compounds by known methods to include functional groups at a variety of positions. As examples, the complexes of the present invention may be modified to include certain reactive groups for preparing a fluorescent labeling reagent, or charged or polar groups may be added to enhance the solubility of the compound in polar or nonpolar solvents or materials.

The present invention also relates to labeling methods wherein rigidized monomethine cyanine complexes of the present invention including at least one functional group at the $R_1$ through $R_7$ positions covalently react with amino, hydroxyl, aldehyde, phosphoryl, sulfhydryl or other reactive groups of proteins or other materials. (As used herein, a phosphoryl group comprises a phosphorous atom and a hydroxyl group linked thereto.) Such other materials which can be labeled by the compounds of the present invention include, but are not limited to, nucleic acid, DNA, RNA, blood cells, microbial materials, and drugs, toxins, particles, plastic or glass surfaces, polymers, and other materials which include amino, hydroxyl, aldehyde, phosphoryl or sulfhydryl reactive groups. Widely available automated DNA sequencers, capillary electrophoresis instruments and fluorescence gel readers are examples of instruments for detecting fluorescently labeled materials.

The present invention also relates to a two-step labeling process in which in a first step one of the reactive complexes of the present invention covalently reacts with and thereby labels a primary component, such as an antibody. Therefore, the functional groups at the $R_1$ through $R_7$ positions of the rigidized monomethine cyanine compound of the present invention are chosen to react with, for example, amino, aldehyde, sulfhydryl, hydroxy, or other groups on the primary component. In a second or staining step of the two-step procedure, the fluorescently labeled primary component is then used as a probe for a secondary component, such as an antigen for which the antibody is specific. When the target of the of the so-labeled antibodies is a cell, the second step of the procedure could be employed to determine the amount of labeled antibodies which are attached to that type of cell. The measurement is made by determining the intensity of the fluorescence of the cells. By this two-step procedure, monoclonal antibodies and other components covalently labeled in the first step with the fluorescent compounds of the present invention could be used as probes for antigens.

The compounds of the present invention can also be employed to determine the concentration of a particular protein or other component in a system. If the number of reactive groups on a protein which can react with a probe is known, the fluorescence per molecule can be known and the concentration of these molecules in the system can be determined by the total fluorescence intensity of the system.

The methods of use of the compounds of the present invention can be employed to quantify a variety of proteins or other materials in a system by labeling all of a mixture of proteins in the system and then separating the labeled proteins by any means such as, for example, chromatographic means. The amount of these separated proteins can then be determined by the fluorescence intensity thereof. In chromatographic detection systems, the location of the dye on the labeled material can also be ascertained.

The compounds of the present invention can also be used to determine the number of different cells tagged by a particular pre-labeled antibody. The determination can be made by tagging a plurality of types of cells in a system, and then separating the tagged cells outside of the system. Also, tagged cells can be separated from non-tagged cells outside of the system.

The fluorescent compounds of the present invention can also be used in a detection method wherein a plurality of the fluorescent compounds are covalently attached to a plurality of different primary components, such as antibodies, each primary component being specific for a different secondary component, such as an antigen, in order to identify each of a plurality of secondary components in a mixture of the secondary components. According to this method of use, each of the primary components is separately labeled with a fluorescent compound having a different light absorption and emission wavelength compared with the dye molecules used for labeling the other primary components. The so-labeled primary components are then added to the preparation containing secondary components, such as antigens, and the primary components are allowed to attach to the respective secondary components for which they are selective. Any unreacted probe materials may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochromaters to select the rays of the excitation wavelength and to select the wavelengths of fluorescence is next employed to determine the intensity of the emission wavelengths corresponding to the fluorescent compounds utilized, the intensity of fluorescence indicating the quantity of the secondary component which has been bound with a particular labeled primary component.

In certain cases a single wavelength of excitation can be used to excite fluorescence from two or more materials in a mixture where each fluoresces at a different wavelength and the quantity of each labeled species can be measured by detecting its individual fluorescence intensity at its respective emission wavelength. If desired, a light absorption detection method can also be employed.

The two-step detection method of the present invention can be applied to any system in which the creation of a primary component-fluorescent dye compound conjugated structure is possible. For example, an appropriately reactive fluorescent compound can be conjugated to a DNA or RNA fragment and the resultant conjugate then caused to bind to a main strand of DNA or RNA to which the conjugated piece is complementary. Appropriate fluorescence detection equipment can then be employed to detect the presence of any bound fluorescent conjugates.

The present invention also relates to the use of the rigidized monomethine cyanine compounds of the present invention as laser dyes.

Specific examples of the groups that can be incorporated at the $R_1$, $R_2$, $R_3$, $R_4$, $R_5$, $R_6$ and $R_7$ of the present invention's compound and the groups with which those R-groups will react are provided in Table 1.

TABLE 1

Possible Reactive Substituents and Functional Reactive Therewith

| Reactive Groups | Corresponding Functional Groups |
|---|---|
| succinimidyl esters | amines |
| anhydrides | amines, alcohols |
| acyl azides | amines |
| isothiocyanates | amines, thiols, alcohols, phenols |
| sulfonyl chlorides, sulfonyl fluorides | amines, phenols, alcohols |
| substituted hydrazines, substituted hydroxylamines | aldehydes, ketones |
| acid halides | amino groups |
| haloacetamides, maleimides | thiols, imidazoles, phenols, amines |
| carobdiimides | carboxyl groups |
| phosphoramidite | alcohol groups |

In addition to those reactive groups listed in Table 1, a number of other possible reactive groups for the present invention's $R_1$, $R_2$, $R_3$, $R_4$, $R_5$, $R_6$ and $R_7$ sites exist. For example, reactive groups which are especially useful for labeling target components with available amino and hydroxy functional groups include:

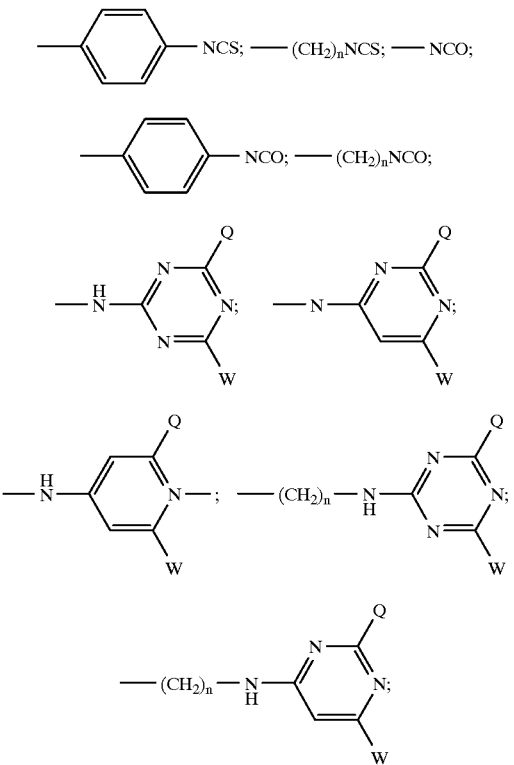

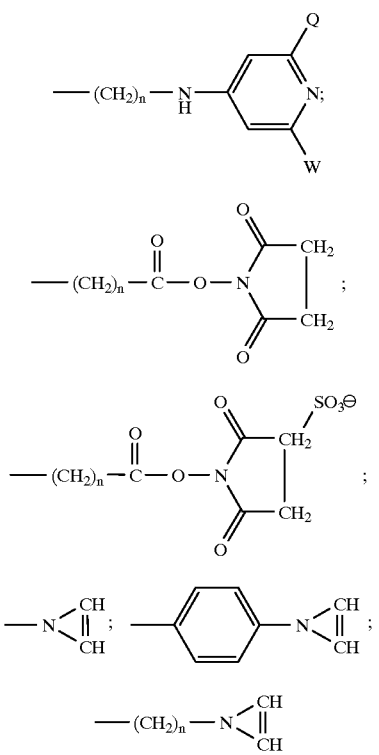

where at least one of Q or W is a leaving group such as I, Br, Cl.

Specific examples of possible $R_1$, $R_2$, $R_3$, $R_4$, $R_5$, $R_6$ and $R_7$ groups that are especially useful for labeling components with available functional groups include:

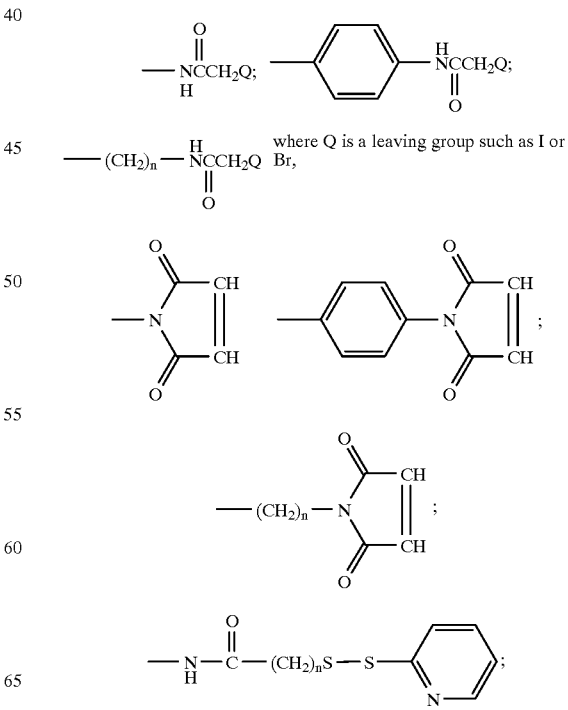

-continued

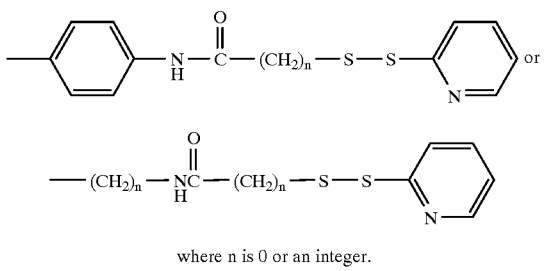

where n is 0 or an integer.

Specific examples of possible $R_1$, $R_2$, $R_3$, $R_4$, $R_5$, $R_6$ and $R_7$ groups that are especially useful for labeling components by light-activated cross linking include:

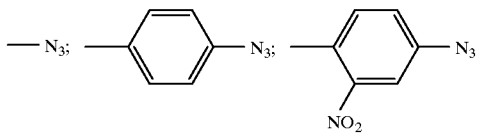

For the purpose of increasing water solubility or reducing unwanted non-specific binding of the labeled component to inappropriate components in the sample or to reduce interactions between two or more reactive chromophores on the labeled component which might lead to quenching of fluorescence, the $R_1$, $R_2$, $R_3$, $R_4$, $R_5$, $R_6$ and $R_7$ groups can be selected from the well known polar and electrically charged chemical groups. Examples of such groups are —E—F where F is hydroxy, sulfonate, sulfate, carboxylate, substituted amino or quaternary amino, and where E is a spacer group such as —$(CH_2)_n$— where n is 0, 1, 2, 3, or 4. Useful examples of —E—F groups include lower alkyl and alkyl sulfonates such as —$(CH_2)_3$—$SO^-$ and —$(CH_2)_4$—$SO_3^-$.

The possible reactive groups provided herein are not meant to be all-inclusive of those groups which can be incorporated at the R sites of the compounds of the present invention. It will be understood that there are various other reactive groups which will covalently or noncovalently associate with sites on material that is to be labeled by the compounds of the present invention. Compounds produced by the incorporation of such other groups at the $R_1$ through $R_7$ positions of the compound of the present invention are intended to be encompassed by the present invention.

DETAILED DESCRIPTION OF THE INVENTION

Figure 1:
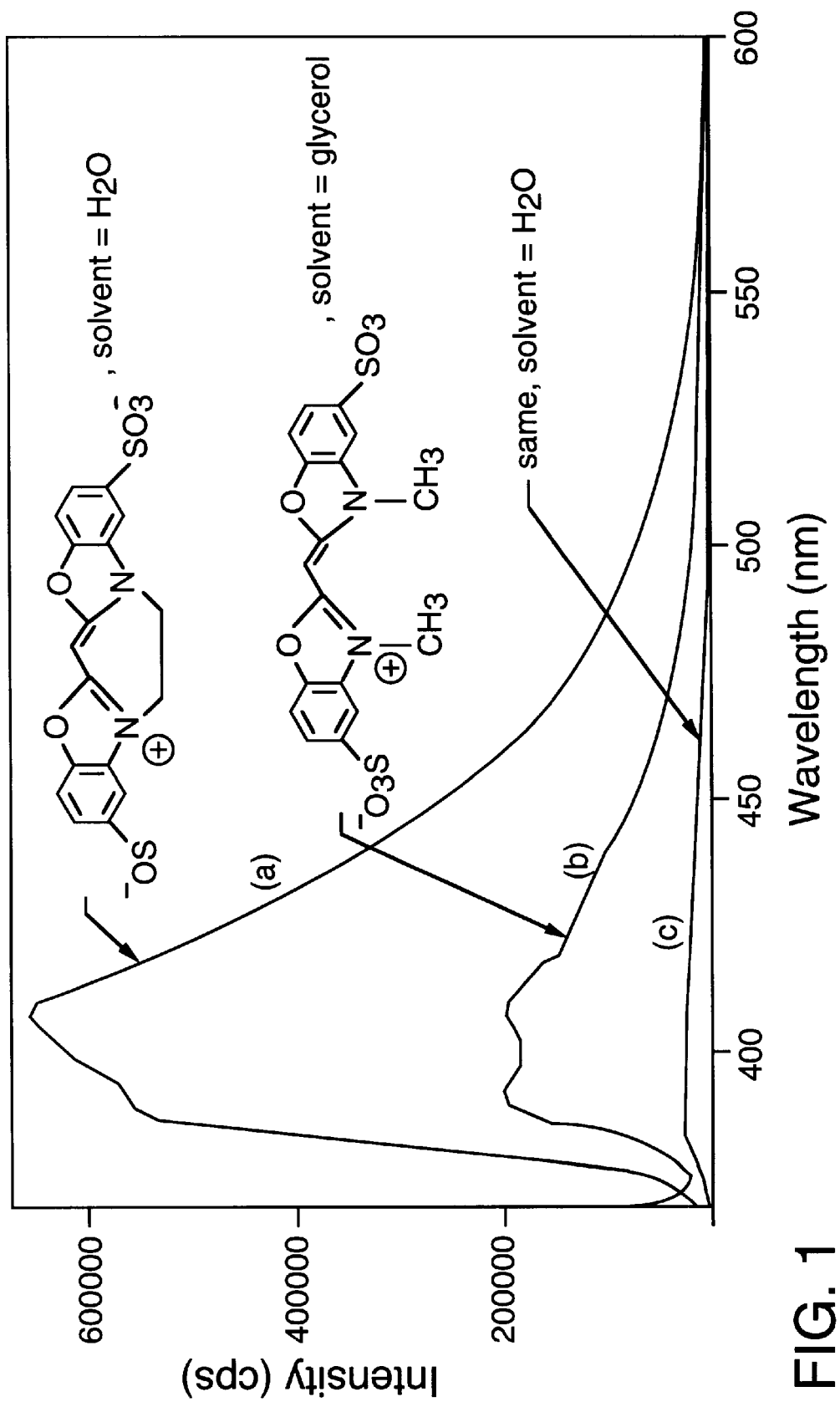
FIG. 1 is a plot of the relative fluorescence spectra of a rigidized monomethine cyanine (curve a), an un-rigidized N,N'-dimethyl-di-2-benzothiazolyl methane in glycerol (curve b), and the same unrigidized molecule in water (curve c), all samples being excited at 364 nm.

There are six general schemes for preparing the carbon-bridged monomethine cyanine complexes of the present invention. Three separate synthetic methods are provided for preparing the symmetric compounds wherein the heterocyclic groups attached by the monomethine bridge are identical. Referring to the schematic formula of the compound of the present invention set forth in the above Summary of the Invention, of the three methods for preparing the symmetric compounds of the invention, two separate methods are provided for producing a symmetric compound having a reactive group on the ethylene bridge in the $R_2$ or $R_3$ positions and one method is provided for preparing compounds having a reactive group in the $R_1$ position on the monomethine bridge.

Three separate synthetic methods are also provided for preparing the asymmetric compounds, two methods wherein a reactive group is in the $R_2$ or $R_3$ position and one method wherein the compound includes a reactive group on the $R_1$ position.

To provide selected R-groups at the sites labeled as $R_4$ through $R_7$ in the schematic formula of the compounds of the present invention provided in the above Summary of the Invention, selected precursors may be employed in the following synthetic pathways already including those R-groups thereon. Alternatively, the rigidized complexes produced from the following pathways can be modified after they are produced to include groups at the R-sites by well known chemical techniques including, for example, sulfonation, nitration, alkylation, acylation, and halogenation. Furthermore, the complexes can be further modified to introduce chemically reactive groups that are understood to fall within the scope of this invention.

I. Preparation of the Symmetric Compounds a. Reactive Group On The Ethylene Bridge (PTS Method)

The general pathway for the PTS (i.e., p-tosylate) method of preparing the symmetric compounds with a reactive group on the ethylene bridge is shown below.

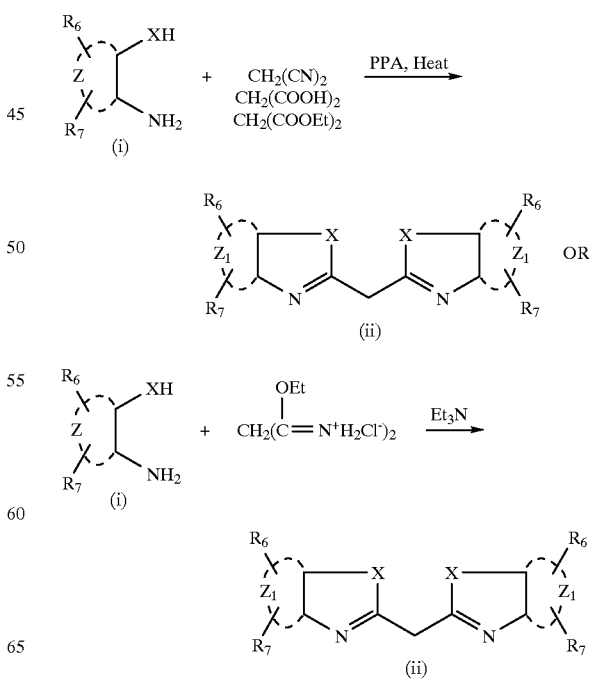

-continued

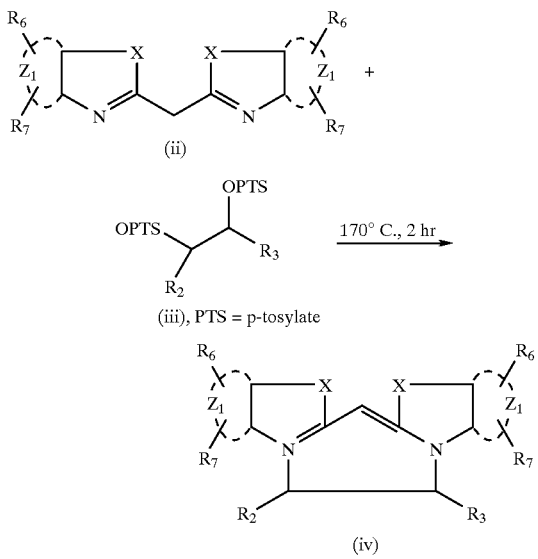

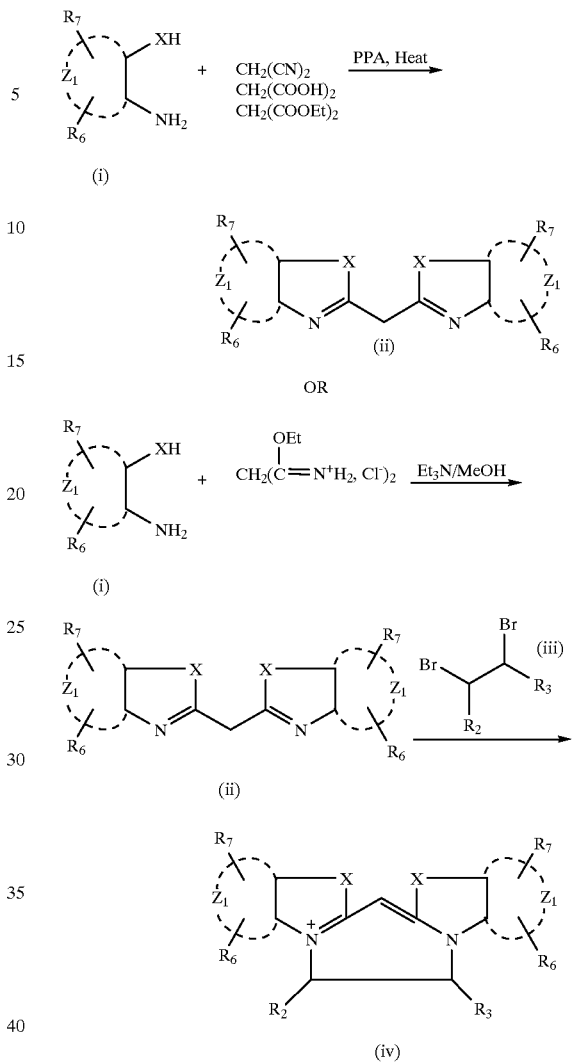

Depending on the final structure desired, X, $Z_1$, $R_2$, $R_3$, $R_6$ and $R_7$ are selected from among the possible structures and groups for those positions listed above.

In the PTS synthetic method for producing the symmetric ethylene-bridged monomethine rigid cyanine dyes of the present invention, the starting material (i) undergoes a condensation reaction in the presence of malononitrile, $CH_2(COOH)_2$, $CH_2(COOEt)_2$, or bis ethylimidate dihydrochloride of malononitrile to provide a bis product (ii) that includes two units of starting material (i) linked by a single carbon atom. The bis product is then quaternized on both nitrogens by polyalkyl 1,2-di-p-tosylate (iii) bearing groups $R_2$ and $R_3$ to form a symmetric monomethine rigidized cyanine dye (iv) having the functional groups $R_2$ and $R_3$ on the ethylene bridge. As an alternative to polyalkyl 1,2-di-p-tosylate, the compound (ii) may be quaternized using any other sulfonic acid in an ester form such as, for example, mesytyl chloride or mesyl chloride.

Compound (iv) may then be hydrolyzed and sulfonated to form a water-soluble dye having one or more sulfonate groups thereon. The sulfonation is not necessary if starting compound (i) carries a sulfonate or sulfonic acid group as one of the substituents. Alternatively, other water soluble groups, for example, hydroxyl, quaternary amino, carbohydrate or polyhdroxylated groups can be introduced. With respect to the preparation of the ethyl bisimidate of malononitrile, reference is made to Muller D., Umbicht G., Weber B., and Pfaltz A., Hel. Chim. Acta. 74, 232–240, (1991). With respect to preparation of polyalkyl 1,2-di-p-tosylate, reference is made to Saito S., Hasegawa, T., Inaba M., and Nishida R., Chem. Letters 1389–1392 (1984) and Lapoworth A., and Mottran E. N., J. Chem. Soc., 1628 (1925). Reference to the overall synthesis is also made to U.S. Pat. No. 2,541,400.

b. Reactive Group On The Ethylene Bridge (Dibromo Method)

The general pathway for the dibromo method of preparing the symmetric compounds with a reactive group on the ethylene bridge is shown below.

Depending on the final structure desired, X, $Z_1$, $R_2$, $R_3$, $R_6$ and $R_7$ are selected from those structures and groups listed above for those positions.

In the dibromo synthetic method for producing the symmetric ethylene bridged monomethine rigid cyanine dyes of the present invention, starting material (i) undergoes a condensation reaction in the presence of malononitrile, $CH_2(COOH)_2$, $CH_2(COOEt)_2$, or bis ethylimidate dihydrochloride of malononitrile to provide a bis product (ii) which includes two units of starting material (i) linked by a single carbon atom. The bis product (ii) is then quaternized on both nitrogens by polyalkyl 1,2-di-bromide (iii) bearing groups $R_2$ and $R_3$ to form a symmetrical monomethine rigidized cyanine dye (iv) having a functional group on the ethylene bridge. Compound (iv) may then be hydrolyzed and sulfonated to form water soluble dye. The sulfonation is not needed if starting compound (i) carries a sulfonate or sulfonic acid group as one of the substituents. Alternatively, other water soluble groups, for example, hydroxyl, quaternary amino, carbohydrate or polyhydroxylated groups, can be introduced.

c. Reactive Group On The Methine Carbon

The general pathway for preparing the symmetric compounds with a reactive group on the methine bridge is shown below.

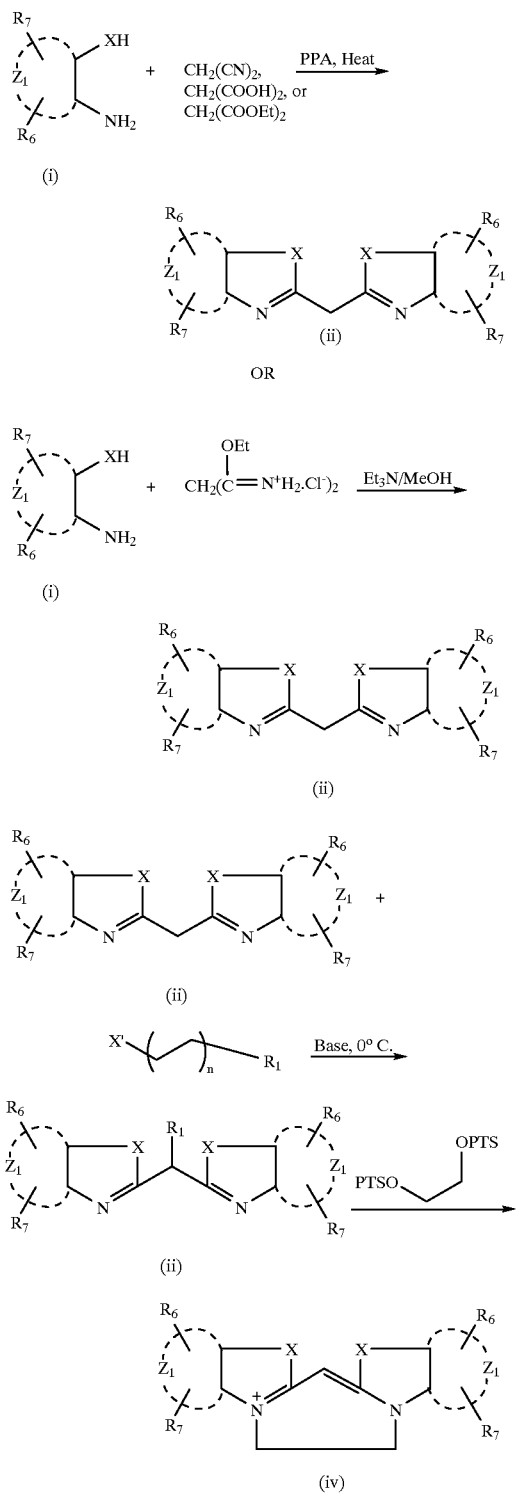

Depending on the final structure desired, X, $Z_1$, $R_6$ and $R_7$ are selected from the structures and groups listed above for those positions.

In the above synthetic method for producing the symmetric ethylene-bridged monomethine rigid cyanine dyes of the present invention, the starting material (i) undergoes a condensation reaction in the presence of either malononitrile, $CH_2(COOH)_2$, $CH_2(COOEt)_2$, or bis ethylimidate dihydrochloride of malononitrile to provide a bis product (ii), which includes two units of starting material (i) linked by a single carbon atom. The bis product (ii) is then reacted with sodium hydride and X'-$(CH_2)_n$-$R_1$ wherein X' is any halogen and n is any whole number from 1-5 so as to incorporate an alkyl chain on the methine group (iii). The bis product (iv) thus obtained is then heated with ethylene glycol-di-p-tosylate to form an asymmetric monomethine rigidized cyanine dye having a functional group on the methine carbon (iv). Compound (iv) may then be hydrolyzed and sulfonated to form a water soluble dye. The sulfonation is not needed if starting compound (i) carries a sulfonate or sulfonic acid group as one of the substituents. Alternatively, other water soluble groups, for example, hydroxyl, quaternary amino, carbohydrate or polyhydroxylated groups, can be introduced.

II. Preparation of the Asymmetric Compounds a. Reactive Group On The Ethylene Bridge (PTS Method)

The general pathway for the PTS method of preparing the asymmetric compounds with a reactive group on the ethylene bridge is shown below.

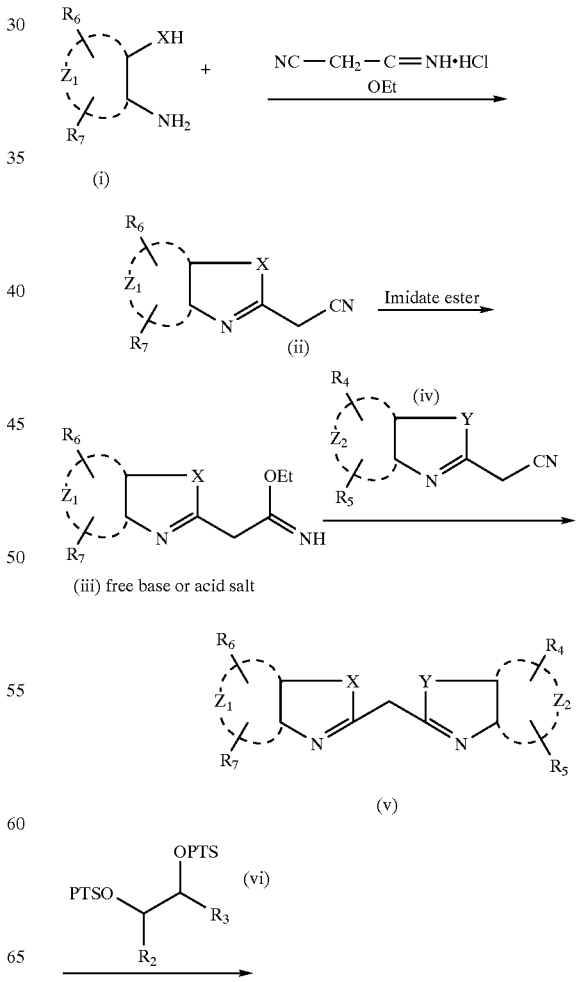

-continued

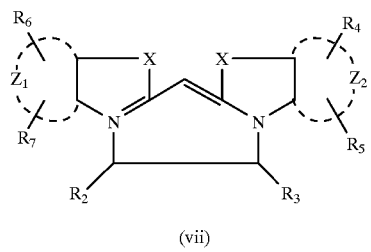

(vii)

Depending on the final structure desired, X, Y, $Z_1$, $Z_2$, and $R_2$ through $R_7$ are selected from those structures and groups listed above for those positions.

In the PTS synthetic method for producing the asymmetric ethylene-bridged monomethine rigid cyanine dyes of the present invention, the starting material (i) undergoes a condensation reaction in the presence of excess malononitrile to provide a product (ii) which is then reacted with an imidate ester to provide a compound (iii). Compound (iii) is reacted with a heterocyclic compound (iv) to provide compound (v). The compound (v) is then quaternized on both nitrogens by polyalkyl 1,2-di-p-tosylate (vi) bearing groups $R_2$ and $R_3$ to form a monomethine rigidized cyanine dye having functional group(s) on the ethylene bridge (vii). As an alternative to polyalkyl 1,2-di-p-tosylate, the compound (vi) may be quaternized using any other sulfonic acid in an ester form such as, for example, mesytyl chloride or mesyl chloride. Compound (vii) may then be hydrolyzed and sulfonated to form a water soluble dye. The sulfonation is not needed if starting compound (i) carries sulfonate or sulfonic acid groups as one of the substituents. Alternatively, other water soluble groups, for example, hydroxyl, quaternary amino, carbohydrate or polyhydroxylated groups can be introduced. Reference is made to U.S. Pat. Nos. 4,064,136 and 2,541,400 for the general scheme for preparing the asymmetric compounds.

b. Reactive Group On The Ethylene Bridge (Dibromo Method)

The general pathway for the dibromo method of preparing the asymmetric compounds with a reactive group on the ethylene bridge is shown below.

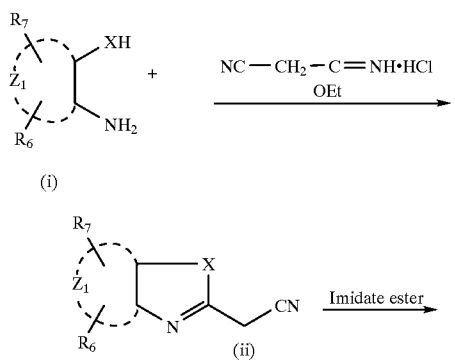

-continued

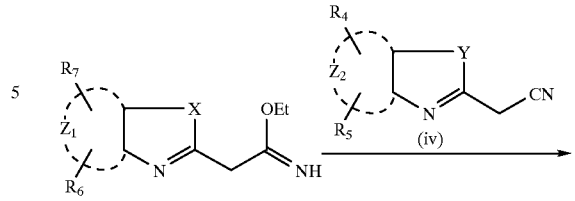

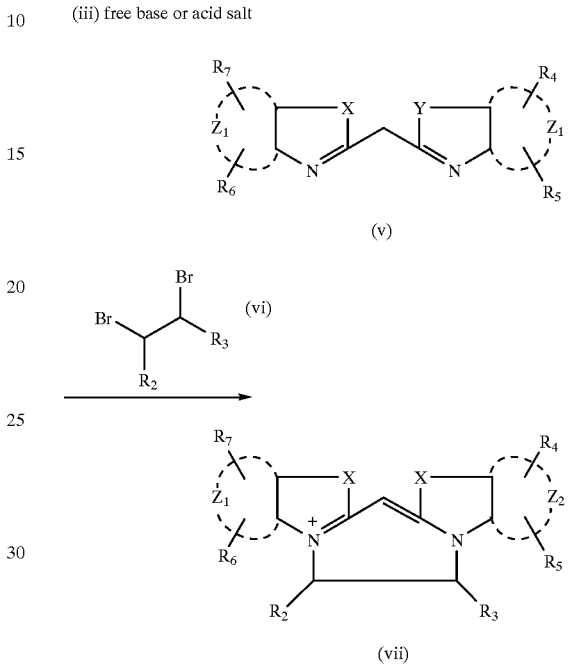

(vii)

Depending on the final structure desired, X, Y, $Z_1$, $Z_2$, and $R_2$ through $R_7$ are selected from those structures and groups listed above for those positions.

In the dibromo synthetic method for producing the asymmetric ethylene-bridged monomethine rigid cyanine dyes of the present invention, the starting material (i) undergoes a condensation reaction in the presence of excess malononitrile to provide a product (ii), which is then reacted with an imidate ester to provide a compound (iii). Compound (iii) is then reacted with a heterocyclic compound (iv) to provide a compound (v). The bis product (v) is then quaternized on both nitrogens by polyalkyl 1,2-di-bromide (vi) bearing groups $R_2$ and $R_3$ to form monomethine rigidized cyanine dye (vii). Compound (vii) may then be hydrolyzed and sulfonated to form a water soluble dye. The sulfonation is not needed if starting compound (i) carries a sulfonate or sulfonic acid group as one of the substituents. Alternatively other water soluble groups, for example, hydroxyl, quaternary amino, carbohydrate or polyhydroxylated groups can be introduced.

c. Reactive Group On The Methine Carbon

The general pathway for preparing the asymmetric compounds with a reactive group on the methine bridge is shown below.

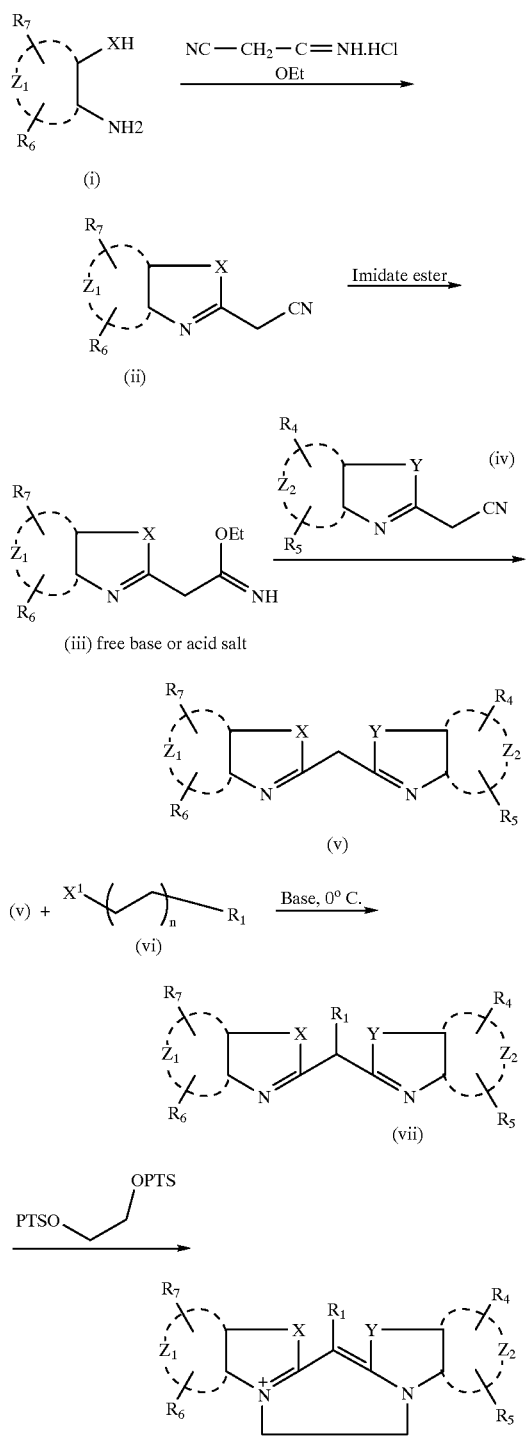

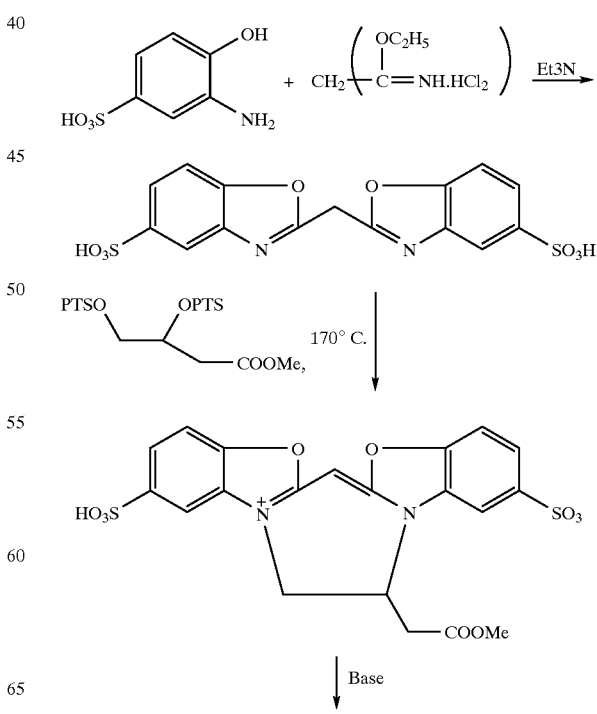

compound (vii). The substituted bis compound (vii) then heated with ethylene glycol-di-p-tosylate to form an asymmetric monomethine rigidized cyanine dye having functional groups on the methine carbon (viii). Compound (viii) may then be hydrolyzed and sulfonated to form water soluble dye. The sulfonation is not needed if a starting compound (i) carries a sulfonate or sulfonic acid group as one of the substituents. Alternatively, other water soluble groups, for example, hydroxyl, quaternary amino, carbohydrate or polyhydroxylated groups, can be introduced.

The carbon-rigidized complexes produced by the above pathways may be produced from precursors that already include R-groups so that the final product also incorporates those R-groups. Alternately, the compounds produced by the above synthetic methods may be chemically modified after production to include desired groups at their R positions. Chemical techniques known to those skilled in the art which may be used to modify the compounds produced by the above reaction pathways to include R-groups at the $R_1$ through $R_7$ positions include, but are not limited to, sulfonation, nitration, alkylation, acylation, and halogenation. It is to be understood that the intermediates in each of the above reaction pathways may also be produced by the methods provided in co-pending application Ser. No. 08/474,056, entitled "Rigidized Monomethine Cyanines".

Following are specific examples of the synthesis of compounds of the present invention and observed spectral data for those compounds.

EXAMPLE A

Compound A was synthesized by the synthetic pathway which is schematically represented below.

Depending on the final structure desired, X, Y, $Z_1$, $Z_2$ and $R_1$ through $R_7$ are selected from those structures and groups listed above for those positions.

In the synthetic method, the starting material (i) undergoes a condensation reaction in the presence of excess malononitrile to provide a product (ii), which is then reacted with imidate ester to provide compound (ii). Compound (ii) is then reacted with a heterocyclic compound (iv) to provide bis compound (v). The bis compound is then reacted with base and X'-$(CH_2)_n$-$R_1$ (vi), wherein X' is any halogen and n is a whole number 1–5, to provide a substituted bis -continued

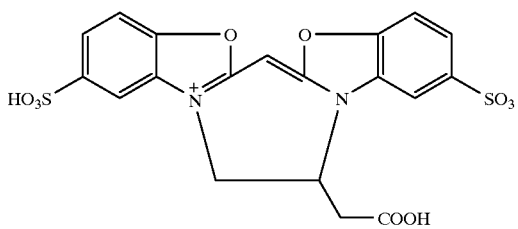

a. Preparation of ethyl bisimidate hydrochloride

The following method is a modification of the method of McElvain et al., (JACS, 71, 40, 1949). Malononitrile (0.66 g, 10 mmol) was dissolved in dry dioxane (5 ml). To this solution was added ethanol (0.92 g, 20 mmol). A 4M solution of HCl in dioxane (5 ml) was injected in one portion into the malononitrile solution. The resulting mixture was stirred for 36 hours at room temperature. The thick white slurry obtained was filtered, washed with at least 3 portion of 50 ml of dry ether and dried under vacuum at room temperature (1–2 h). The yield of ethyl bisimidate hydrochloride was 93%.

b. Preparation of disulfo-3,3'-oxacyanine-triethylamine salt

To a suspension of 3-amino-4-hydroxybenzenesulfonic acid (18.9 g, 0.1 mol) in methanol (100 ml) was added triethylamine (11.2 g, 0.11 mol). The solution was concentrated (50 ml) and cooled. A brown crystalline product of triethylamine salt was obtained which melted at 200° C. with decomposition. The yield was 85–90% of the theoretical.

Triethylamine salt (29 g, 0.1 mol) was suspended in dry methanol (200 ml). Freshly prepared diethyl-bisimidatedihydrochloride (11.5 g, 0.05 mol) was added to the suspension and the mixture was heated to reflux. Within 5 minutes the solution became clear. Heating was continued for 2 hours after which the solution became turbid. The reaction mixture was then cooled and brown crystals of Compound A were separated, filtered off (12 g). The crystals melted at 170–175° C.

c. Preparation of alpha-carboxymethyl-disulfo-3,3'-ethylene-oxacyanine

Compound (A)(100 mg, 0.2 mmol) and methyl-3,4-di-p-tosylbutyrate (mg, 0.2 mmol) were thoroughly mixed and heated slowly at 185° C. (oil bath temperature) for 20 minutes. The resulting dark brown mass was titrated with 0.2 mmol of triethylamine and isopropanol (20 ml) until a free powder was obtained (100 mg). The crude product showed three bright spots in C18 TLC (10% methanol-water). The product was chromatographed on a C18 reversed-phase column with water-methanol mixture as eluent. A compound with Rf=0.75 was recovered from the solvent to yield a silver colored powder (10 mg).

Figure 2:
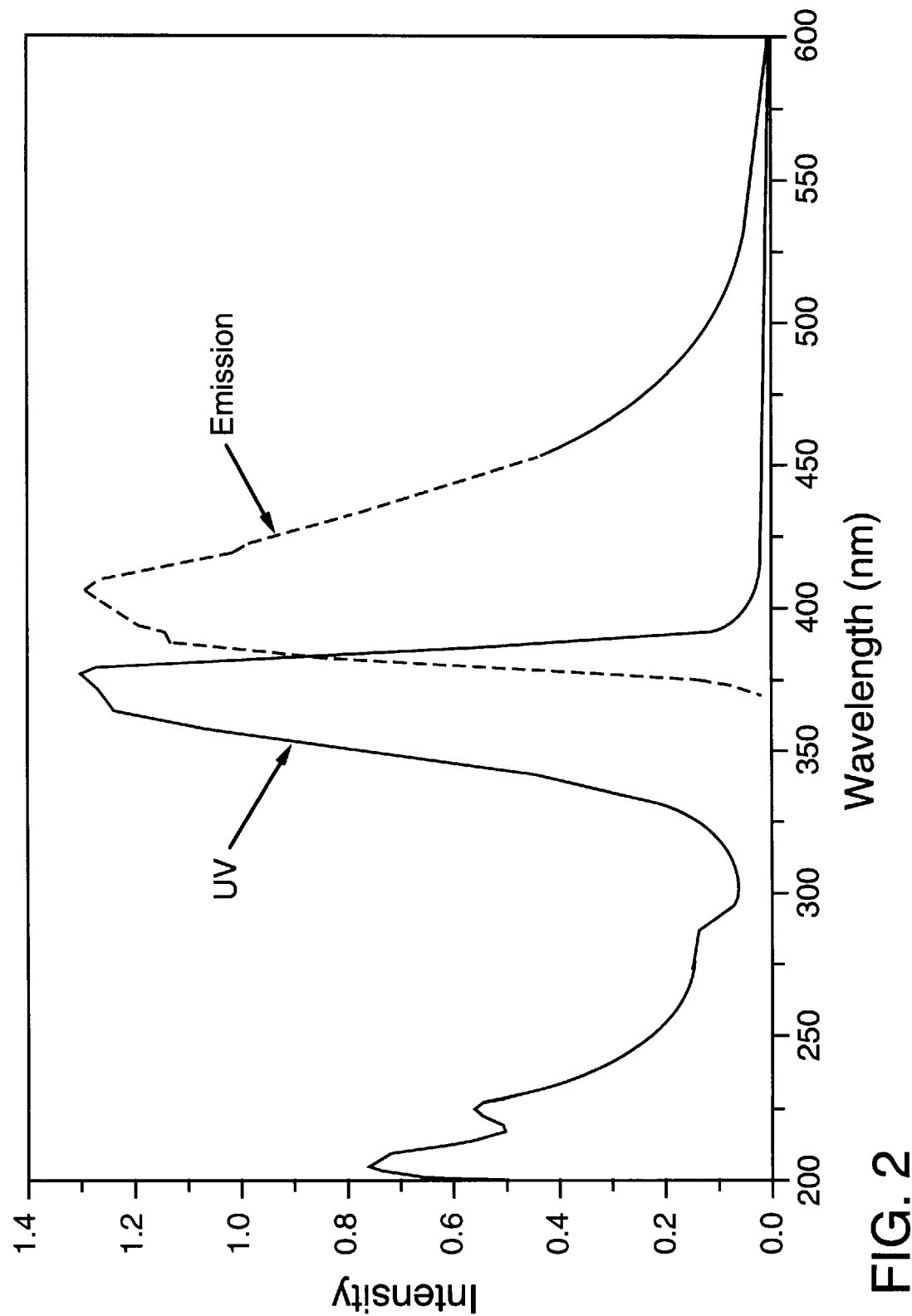
FIG. 2 is the UV absorption spectrum and the emission spectrum for the compound of Example A.

As shown in FIG. 2, the UV spectra showed an absorption maximum at 364 nm and an emission maximum at 386 nm when excited at 360 nm. Quantum yield was 0.8 with quinine sulfate as the standard. During the quaternization reaction some methyl ester was hydrolyzed to give a free dye acid. This dye acid was used to prepare succinimidyl ester.

d. Dye conjugation with an antibody

The acid was converted to its succinimidyl ester according to the procedure and was dissolved in 100 microliters dry dimethylformamide containing 10 microliters pryidine. Excess (10 mg) disuccinimidyl carbonate was added and the mixture was heated at 65–70° C. for 2 hours under a nitrogen atmosphere. After completion of the reaction, dry diethyl ether (50 ml) was added. The precipitated ester was filtered and dried in a vacuum for 1 hr.

Figure 3:
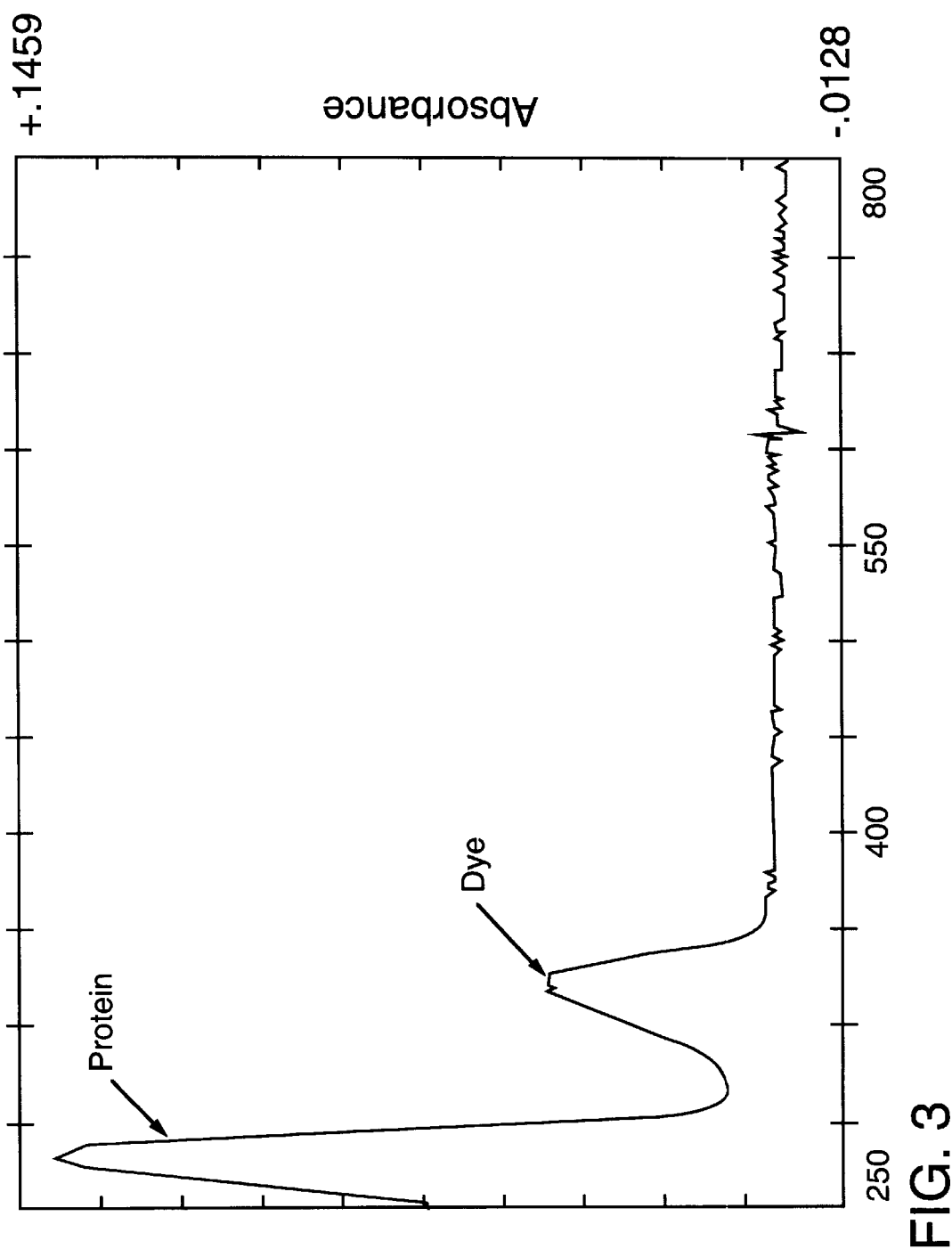
FIG. 3 is the UV absorption spectrum of the compound of Example A conjugated to IgG sheep antibody.

The dried ester (approximately 1 mg) was dissolved in DMF (50 microliters) and 10 microliters of this stock solution was allowed to react for 30 minutes with 1 mg of Sheep IgG protein dissolved in 250 ml carbonate-bicarbonate buffer (pH 9.4). The dye- antibody conjugate was separated from unreacted dye on a size exclusion column (Sephadex G-50) using phosphate saline buffer solution (pH 7) as eluent. The absorption and emission spectra of the dye-antibody conjugate are shown in FIG. 3. The protein absorbed at 280 nm (0.1387 absorbance units) and the dye absorbed at 372 nm (0.04257 absorbance units).

EXAMPLE B

The synthesis of compound B proceeded by a synthetic pathway schematically represented below.

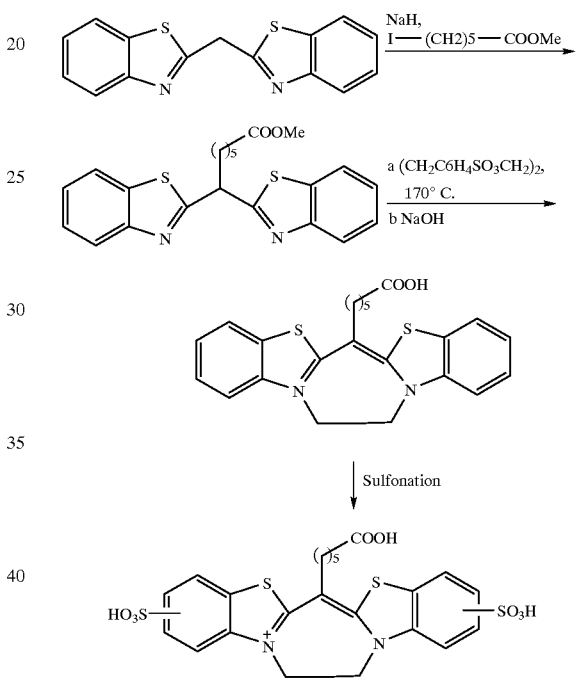

a. Synthesis of methyl ester of meso-bis-methine benzothiazolyl-hexanoic acid

A sodium hydride slurry in mineral oil (80%, 30 mg) was quickly transferred to a flame-dried 25 ml round bottom flask fitted with a stir bar. Dry, freshly distilled THF (4 ml) was then added. In another flask a weighed quantity of bisbenzothiazolyl methane (0.28 g, 1 mmol) was dissolved in 1.5 ml dry THF. This solution was added dropwise to the stirred sodium hydride slurry. Hydrogen gas evolved during the reaction was carefully vented off. After effervescence ceased, the reaction mixture was stirred for 0.5 hour.

Next, methyl iodohexanoate (0.256 g, 1 mmol) was added dropwise to the reaction mixture. Within minutes of addition, the reaction mixture became turbid due to precipitation of sodium iodate. Stirring was continued for 2 hours, after which the solids were separated either by centrifugation or filtration. The filtrate was evaporated to a green oil which was then diluted with methanol (2 ml) and left undisturbed for 0.5 hour, when a yellow-green solid separated out. Further cooling yielded more solid. After filtration and drying, 0.1 g solids were recovered providing a yield of 28%.

b. Synthesis of Compound B

The compound of step a. (100 mg, 0.24 mmol) and ethylene glycol di-p-tosylate (100 mg, 27 mmol) were thoroughly mixed and heated slowly at 185° C. (oil bath temperature) for 20 minutes. The resulting dark brown mass was titrated with 0.2 mmol of triethylamine and until a free powder was obtained (500 mg). The crude product was chromatographed on a C18 reversed-phase column with water-methanol mixture as eluent. UV spectra of Compound B recorded in water, 0.1 N HCl, and 0.1N NaOH showed an absorption maximum at 364 nm and an emission maximum at 386 nm when excited at 360 nm. The quantum yield was 0.8 with quinine sulfate as standard. In separate testing, Compound B was tested in PBS and had an absorbance maximum of 454 nm, excitation wavelengths of 418 and 432 nm, an emission wavelength of 472 a quantum yield of 0.28 Using Coumarin 30 in ethanol as the reference standard) and a Stoke's shift of 18 nm.

Compound B conjugated to sheep IgG protein and in PBS solvent was found to have an absorbance maximum of 456 nm, excitation wavelengths of 418 and 432 nm, an emission wavelength of 472 a quantum yield of 0.15 Using Coumarin 30 in ethanol as the reference standard) and a Stoke's shift of 16 nm.

c. Sulfonation of Compound B

This compound may be sulfonated using the same procedure as set forth for compound C below.

EXAMPLE D

Compound D (3,3'-ethylene-6-sulfothia-(5'-carboxymethyl, 6'-sulfo)-oxacyanine) was synthesized according to the following scheme:

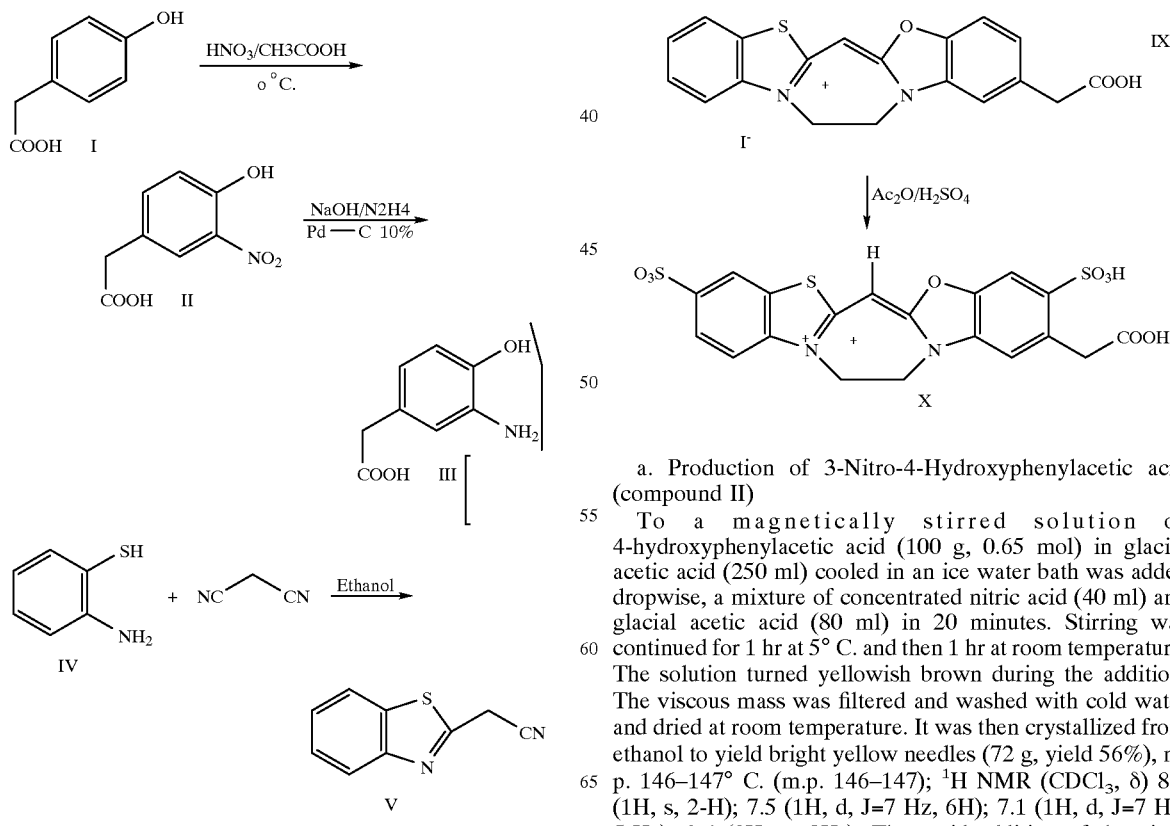

a. Production of 3-Nitro-4-Hydroxyphenylacetic acid (compound II)

To a magnetically stirred solution of 4-hydroxyphenylacetic acid (100 g, 0.65 mol) in glacial acetic acid (250 ml) cooled in an ice water bath was added dropwise, a mixture of concentrated nitric acid (40 ml) and glacial acetic acid (80 ml) in 20 minutes. Stirring was continued for 1 hr at 5° C. and then 1 hr at room temperature. The solution turned yellowish brown during the addition. The viscous mass was filtered and washed with cold water and dried at room temperature. It was then crystallized from ethanol to yield bright yellow needles (72 g, yield 56%), m. p. 146–147° C. (m.p. 146–147); $^1$H NMR (CDCl$_3$, δ) 8.0 (1H, s, 2-H); 7.5 (1H, d, J=7 Hz, 6H); 7.1 (1H, d, J=7 Hz, 5-H ); 3.6 (2H, s, CH$_2$). The rapid addition of the nitric acid/acetic mixture should be avoided to prevent formation of 3,5-dinitro-4-hydroxyphenylacetic acid.

b. Production of 3-amino-4-hydroxyphenylacetic acid (compound III)

Compound III was synthesized according to the method of Zupancic and Trpin *J. Prac. Chem.* 33, 307–308 (1966); CA 66, 37580c. To a stirred solution of sodium hydroxide solution (1 g in 40 ml) in a round bottom flask was added 3-nitro-4-hydroxyphenylacetic acid (4.93 g, 0.025 mol). The solid dissolved at once giving an orange color solution. 10% Pd-C (50 mg) was added followed by dropwise addition of hydrazine monohydrate (3.25 ml). After the completion of the addition (5 minutes), the mixture was heated at 60° C. for 1.5 hr. The temperature was raise to reflux and heating continued for additional 0.5 hr. The solution appeared clear with Pd-C suspended in it. The solution was filtered hot, concentrated to half of the volume and then cooled. The solution was acidified carefully to pH 4–5 with acetic acid. The white precipitate separated after cooling was filtered off and washed with ethanol. m.p. 225–227° C. lit[2]. 229–230° C. (3.4 g, yield 30%). $^1$H NMR ($D_2O$, δ) 7.9 (1H, d, j=7 Hz, 6-H); 7.8 (s, 1H, 2-H); 7.65 (1H, d, J=7 Hz, 5-H); 3.4 (2H, s, $CH_2COOH$).

c. Production of 2-Cyanomethylbenzothiazole (compound V)

This compound was prepared according to a method of Saito et.al, *Synthesis* 210–11 (1983). A mixture of 2-aminothiophenol (10 mmol), malanonitrile (10 mmol) and glacial acetic acid (10 mmol) in ethanol was stirred at room temperature for 12–15 hr. The yellow crystalline product was recovered after filtration and drying (Yield 82%), IR (KBr) 2227 $cm^{-1}$.

d. Production of 2-benzothiazolyl-2'-(5'-carboxymethylbenzoxazolyl) methane (compound VIII)

A mixture of 2-cyanomethylbenzothiazole (1.74 g, 0.01 mol) and sodium methoxide (0.5 g, 0.01 mol) in anhydrous methanol (50 ml) was stirred at room temperature for 15 hr. The orange powder (VII) obtained was used for the next reaction without separation. Thus, to this mixture a drop of acetic acid is added to neutralize sodium methoxide. 3-amino-4-hydroxyphenylacetic acid (1.67 g, 0.01 mol) was added all at once and the mixture was heated to reflux. After 4 hr. methanol was and the residue (3.4 g) was purified by flash chromatography on silica gel column (50 g) using chloroform/methanol mixture as eluant. Yellowish green crystals from ethanol, m.p. 182–184° C., (0.75 g, yield 23%). $^1$H NMR (DMSO d6, δ) 8.1 (1H, d, J=7 Hz), 7.9 (1H, d, J=7 Hz), 7.62 (1H, d, J=7 Hz), 7.6 (1H, s), 7.4–7.55 (2H, m), 7.3 (1H, d, J=7 Hz), 5.0 (2H, s, $CH_2$-bridge), 3.7 (2H, s. $CH_2COOH$)

e. Production of 3,3'-ethylene-thia-(5'-carboxymethyl) oxacyanine (compound IX)

324 mg (1 mmol) Of acid (VIII) and 370 mg (1 mmol) of ethylene di-p-toluenesulfonate were heated together for 4 hr, at 170° C. The resulting solid yellow product was cooled and 100 ml acetone was added to it followed by 2 ml of triethylamine. The solution was evaporated to dryness, washed with ether to remove excess triethylamine. The solid dark brown mass was then dissolved in methanol. Sodium iodide dissolved in 10 ml of hot methanol was added to convert 3,3'-ethylene-cyanine p-toluenesulfonate to the cyanine iodide. The solvent was removed and the entire mass dissolve in a solution of 10% methanol in chloroform, followed by flash column chromatography on silica gel using chloroform-methanol mixture as eluant. Two yellow products appeared very bright in UV light and were isolated. The compound 1 (20 mg, rf 0.3, silica gel 10% methanol-chloroform) is not characterized. The compound 2 (150 mg, rf 0.1, silica gel 50% methanol-chloroform) is characterized as the desired dye (IX). It was repurified on a reversed phased (C18) column using water-methanol mixture as an eluant. $^1$H NMR (DMSD $d_6$, δ) 8.2 (1H, d, J=7 Hz), 7.9 (1H, d, J=7 Hz), 7.45–7.6 (3H, m), 7.4 (1H, t, ), 7.3 (1H, d, J=7 Hz), 6.5 (1H, s, CH-bridge), 4.9–4.7 (4H, broad m, C$\underline{H}_2$-CH2), 3.4 (2H, s, $CH_2COOH$). UV (methanol) $\lambda_{max}$ 410 nm, ε 61,000, $Em_{max}$ 420, Φ0.24 in water and 0.82 in methanol, based on coumarin 30 as standard.

f. Production of 3,3'-ethylene-6-sulfothia-(5'-carboxy methyl)-6'-sulfooxacyanine (compound X)

The dye IX (100 mg) was dissolved in a mixture of concentrated sulfuric acid (1 ml) and acetic anhydride (1 ml) and heated to 140° C. for 1 hr. The mixture was cooled and the dark brown mass was titrated with acetone (50 ml). The solution was filtered and the solid obtained was chromatographed on reversed phase C18 with water as solvent. (Rf 0.8, C18, water), $^1$H NMR ($D_2O$, δ) 8.2 (1H, s, 7-H) 8.1 (1H, s, 7'-H), 7..95 (1H, d, J=7 Hz, 5-H), 7.75 (1H, d, J=7 Hz, 4-H), 7.45(1H, s, 4'-H), 6.3 (1H, s, CH-bridge), 4.9–4.7 (4H, broad m, $CH_2$-$CH_2$, merged in a water signal), 4.0 (2H, s, $CH_2COOH$). UV (methanol) $\lambda_{max}$ 414 nm, ε 70,000, $Em_{max}$ 420 nm, Φ 0.60 (water) based on coumarin 30 as standard.

g. Dye Conjugation Experiments

The compounds labeled as IX (nonsulfonated dye compound) and X (disulfonated dye compound) were used to label protein. Both compounds IX and X were converted into a succinimidyl ester according to the procedure described in Mujumdar et al. Bioconjugate Chem. 4, 105 (1993). The dye (1 mg) was dissolved in 100 μl dry dimethylformamide containing 10 μl pyridine. Disuccinimidyl carbonate (7 mg) was added to this mixture and heated at 65–70° C. for 2 hr under a nitrogen atmosphere. After completion of the reaction, the solvents were removed under reduced pressure at 50° C. The dried succinimidyl ester was dissolved in 100 μl dry DMF and 10 μl of this stock solution was allowed to react for 30 minutes with 1 mg of Sheep IgG dissolved in 250 μl carbonate/bicarbonate buffer (pH 9.4). The dye antibody conjugate was separated from unreacted dye on a size exclusion column (Sephadex G-50) using phosphate saline buffer solution (pH 7) as eluant. The following spectral data were obtained for each of conjugated and unconjugated compounds IX and X in various solvents.

| Compound | Solvent | Absorbence (max) | Excitation (nm) | Emission (nm) | QY | Stoke's shift |
|---|---|---|---|---|---|---|
| IX | MeOH | 410 | 384 | 444 | 0.82 | 34 |
| IX | Water | 408 | 384 | 440 | 0.24 | 32 |
| IX-IgG | PBS | 412 | 384 | 418 | 0.08 | 6 |
| X | Water | 414 | 384 | 422 | 0.6 | 8 |
| I-IgG | PBS | 414 | 384 | 424 | 0.34 (*) | 10 |

*The dye-IgG was at room temperature for three days.

The dye (compound IX in the schematic depicting the synthesis of Compound D) was also used in experiments to tag DNA. 5-aminopropargyl-2-deoxy-cytosine-5-triphosphate was incorporated into a sequence of DNA by a standard nick translation reaction. The resulting DNA containing aliphatic amino groups was purified by ethanol precipitation, dissolved in borate-EDTA buffer, and stored at −20° C. Fluorescent DNA was formed by reacting this amino-DNA (about 1 microgram) with a fluorescent labeling dye IX (N-hydroxy succinimidyl ester derivative of a blue-fluorescing cyanine dye). 1 μg aminopropargyl DNA in 25 μl buffer was diluted with 25 μl formamide, heated at 77° C. for 5 minutes to denature the DNA into single stranded form, then immediately chilled on ice to inhibit reformation of double-stranded DNA. This cold solution was diluted with an equal volume of carbonate buffer (0.1M, pH 9.2). The reactive dye (about 10 mmoles in 1 μl dimethyl formamide) was added to the DNA and the mixture was incubated at room temperature for 1 hour. The DNA was precipitated with ammonium acetate/ethanol using a standard protocol, washed twice with ice-cold 70% ethanol, then redissolved in TRIS-EDTA buffer. The fluorescent DNA product was analyzed by agarose gel electrophoresis and visualized using standard UV transillumination.

EXAMPLE E AND F

Using the synthetic pathways of the present invention, the inventors provided the following Compounds E and F:

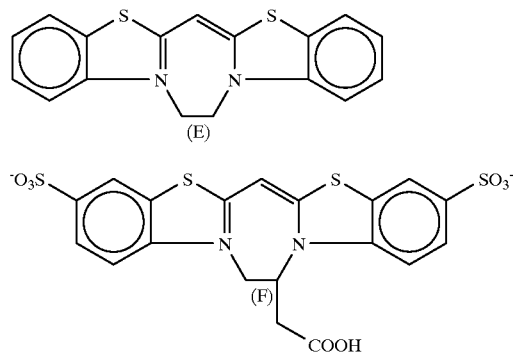

The compounds exhibited the following spectral properties in the indicated solvents. Compound F was also conjugated to sheep IgG protein and exhibited the indicated spectral properties. The quantum yields were determined using Coumarin 30 in ethanol as the reference standard.

| COMPOUND | SOLVENT | ABS MAX | EX WAV | EM WAV | QY | Etches Shift |
|---|---|---|---|---|---|---|
| DYE E | Methanol | 438 | 418 | 450 | 0.81 | 12 |
| DYE E | Pbs | | 418 | 450 | 0.61 | |
| DYE F | Methanol | 440 | 418 | 450 | 1.216 | 10 |
| DYE F | Water | 450 | 418 | 472 | 0.7 | 22 |
| DYE F w/IgG | Pbs | 450 | 418 | | | |

COVALENT LABELING OF A GLASS SURFACE

Alkoxysilanes are known to react with glass surfaces. One such reagent, 3-aminopropyltrimethoxysilane, is known to coat porous glass beads to form the aminopropyl derivative of the glass for use as an absorbent for affinity chromatography. See *Biochem. Biophys. Act.,* 212, 1 (1970); *J. Chromotography,* 97, 39 (1974). The inventors have adapted that procedure to stain glass slides with fluorescent dye compounds of the present invention.

Gold Seal Micro slides (Becton-Dickenson) were washed in distilled water and acetone. The slides were then treated with 10% (v/v) solution of 3-aminopropyltrimethoxysilane (Sigma Chemicals) in xylene for thirty minutes. The slides were then rinsed in absolute ethanol (to remove the xylene), rinsed in water, and air-dried. A solution (approximately 200 microliters) of carbonate/bicarbonate buffer (pH 9.4) was placed at the center of each slide along with 20 microliters of a solution of a dye of the present invention dissolved in dimethylformamide (approximately 2 mg dye/100 microliters dimethylformamide). The dye compound used is the following succinimidyl ester monomethine cyanine compound:

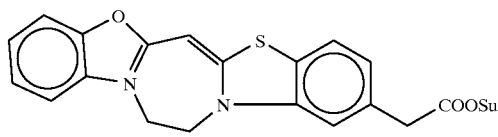

The succinimidyl ester derivative was prepared by known methods using the method generally described in U.S. Pat. No. 5,268,486. The slides were incubated for 20 minutes before being rinsed with distilled water. In this way, the succinimidyl ester dye compound was attached covalently to the slides' glass surface. The presence of covalently-attached dye on the glass surfaces was detected by fluorescence spectrophotometry.

What is claimed:
1. A fluorescent molecule having the structure

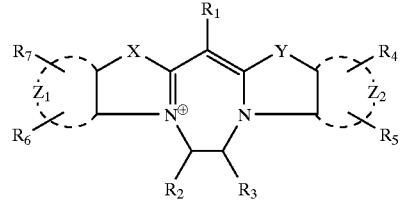

wherein:
X is >N—W—P, where N is nitrogen;
Y is selected from the group consisting of —C(CH$_3$)$_2$—, oxygen, sulfur, selenium, —CH=CH—, and ≧N—W—P where N is nitrogen;
dotted lines Z$_1$ and Z$_2$ represent the atoms necessary to complete a structure selected from the group consisting of one ring, two fused rings, and three fused rings, each said ring having six carbon atoms;
R$_1$ through R$_7$ are individually selected from the group consisting of —P and —W—P wherein:
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
P is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramadite, alkylimidate, arylimidate, acid halide, substituted hydrazines, substituted hydroxylamines, carbodiimides; and electron donating and withdrawing groups that shift the absorption and emission wavelengths of the fluorescent molecule.

2. A fluorescent molecule having the structure

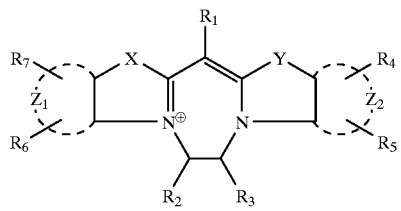

wherein:

X is >N—W—P, where N is nitrogen;

Y is selected from the group consisting of —C(CH$_3$)$_2$—, oxygen, sulfur, selenium, —CH=CH—, and >N—W—P where N is nitrogen;

dotted line $Z_1$ represents the atoms necessary to complete a single ring having five or six atoms comprising carbon atoms and, optionally, no more than two atoms selected from oxygen, nitrogen and sulfur;

dotted line $Z_2$ represents the atoms necessary to complete a structure selected from the group consisting of one ring, two fused rings, and three fused rings, each ring having five or six atoms, and each ring comprising carbon atoms and, optionally, no more than two atoms selected from oxygen, nitrogen and sulfur;

$R_1$ through $R_7$ are individually selected from the group consisting of —P and —W—P wherein:

W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and P is a group conferring desired properties and is selected from the group consisting of:

neutral groups that reduce water solubility selected from the group consisting of hydrogen and halogen atoms;

polar groups that increase water solubility selected from the group consisting of amide, sulfonate, sulfate, phosphate, quaternary ammonium, hydroxyl and phosphonate;

functional groups that can be used in labeling reactions selected from the group consisting of amino, hydroxyl, sulfhydryl, carboxyl and carbonyl;

reactive groups selected from the group consisting of succinimidyl ester, isothiocyanate, isocyanate, iodoacetamide, maleimide, sulfonyl halide, phosphoramadite, alkylimidate, arylimidate, acid halide, substituted hydrazines, substituted hydroxylamines, carbodiimides; and electron donating and withdrawing groups that shift the absorption and emission wavelengths of the fluorescent molecule.

3. A fluorescent molecule having the structure

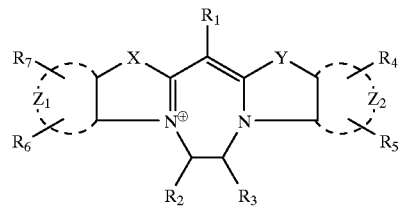

wherein:

X is >N—W—P, where N is nitrogen;

Y is selected from the group consisting of —C(CH$_3$)$_2$—, oxygen, sulfur, selenium, —CH=CH—, and >N—W—P where N is nitrogen;

dotted line $Z_1$ represents the atoms necessary to complete two fused rings, each ring having five or six atoms, each ring comprising carbon atoms and, optionally, no more than two atoms selected from oxygen, nitrogen and sulfur;

dotted line $Z_2$ represents the atoms necessary to complete a structure selected from the group consisting of one ring, two fused rings, and three fused rings, each ring having five or six atoms, and each ring comprising carbon atoms and, optionally, no more than two atoms selected from oxygen, nitrogen and sulfur;

$R_1$ through $R_7$ are selected from the group consisting of —P and —W—P wherein:

W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and P is a group conferring desired properties and is selected from the group consisting of:

neutral groups that reduce water solubility selected from the group consisting of hydrogen and halogen atoms;

polar groups that increase water solubility selected from the group consisting of amide, sulfonate, sulfate, phosphate, quaternary ammonium, hydroxyl and phosphonate;

functional groups that can be used in labeling reactions selected from the group consisting of amino, hydroxyl, sulfhydryl, carboxyl and carbonyl;

reactive groups selected from the group consisting of succinimidyl ester, isothiocyanate, isocyanate, iodoacetamide, maleimide, sulfonyl halide, phosphoramadite, alkylimidate, arylimidate, acid halide, substituted hydrazines, substituted hydroxylamines, carbodiimides; and electron donating and withdrawing groups that shift the absorption and emission wavelengths of the fluorescent molecule.

4. A fluorescent molecule having the structure

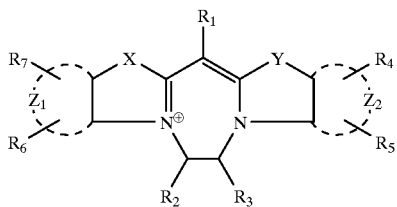

wherein:
X is >N—W—P, where N is nitrogen;
Y is selected from the group consisting of —C(CH$_3$)$_2$—, oxygen, sulfur, selenium, —CH=CH—, and >N—W—P where N is nitrogen;
dotted line $Z_1$ represents the atoms necessary to complete three fused rings, each ring having five or six atoms, each ring comprising carbon atoms and, optionally, no more than two atoms selected from oxygen, nitrogen and sulfur;
dotted line $Z_2$ represents the atoms necessary to complete a structure selected from the group consisting of one ring, two fused rings, and three fused rings, each ring having five or six atoms, and each ring comprising carbon atoms and, optionally, no more than two atoms selected from oxygen, nitrogen and sulfur;
$R_1$ through $R_7$ are selected from the group consisting of —P and —W—P wherein:
W is a linker selected from the group consisting of branched alkyl chains of 1–27 carbon atoms, straight alkyl chains of 1–27 carbon atoms, monoethers containing 2–20 carbon atoms, and polyethers containing 2–20 carbon atoms; and
P is a group conferring desired properties and is selected from the group consisting of:
neutral groups that reduce water solubility selected from the group consisting of hydrogen and halogen atoms;
polar groups that increase water solubility selected from the group consisting of amide, sulfonate, sulfate, phosphate, quaternary ammonium, hydroxyl and phosphonate;
functional groups that can be used in labeling reactions selected from the group consisting of amino, hydroxyl, sulfhydryl, carboxyl and carbonyl;
reactive groups selected from the group consisting of succinimidyl ester, isothiocyanate, isocyanate, iodoacetamide, maleimide, sulfonyl halide, phosphoramadite, alkylimidate, arylimidate, acid halide, substituted hydrazines, substituted hydroxylamines, carbodiimides; and
electron donating and withdrawing groups that shift the absorption and emission wavelengths of the fluorescent molecule.

* * * * *